US008518453B2

(12) United States Patent
Vembu

(10) Patent No.: US 8,518,453 B2
(45) Date of Patent: Aug. 27, 2013

(54) COMPOSITIONS AND METHODS FOR THE PREVENTION AND TREATMENT OF METABOLIC DISEASES

(76) Inventor: Rajan V. Vembu, Madison, WI (US)

( * ) Notice: Subject to any disclaimer, the term of this patent is extended or adjusted under 35 U.S.C. 154(b) by 131 days.

(21) Appl. No.: 12/890,090

(22) Filed: Sep. 24, 2010

(65) Prior Publication Data
US 2011/0189337 A1 Aug. 4, 2011

Related U.S. Application Data

(60) Provisional application No. 61/245,505, filed on Sep. 24, 2009.

(51) Int. Cl.
A61K 35/20 (2006.01)
(52) U.S. Cl.
USPC .......................................................... 424/535
(58) Field of Classification Search
None
See application file for complete search history.

(56) References Cited

U.S. PATENT DOCUMENTS

| 3,615,664 | A | * | 10/1971 | Francis | 426/239 |
|---|---|---|---|---|---|
| 3,896,241 | A | * | 7/1975 | Malaspina et al. | 426/271 |
| 5,268,190 | A | * | 12/1993 | Gerhard | 426/580 |
| 5,639,501 | A | | 6/1997 | Vembu et al. | |
| 5,912,032 | A | * | 6/1999 | Komatsu et al. | 426/74 |
| 6,139,901 | A | * | 10/2000 | Blazey et al. | 426/656 |
| 6,740,334 | B2 | | 5/2004 | Takada et al. | |
| 7,247,331 | B2 | * | 7/2007 | Souppe | 426/491 |
| 2003/0026845 | A1 | * | 2/2003 | Etzel et al. | 424/535 |
| 2004/0052860 | A1 | * | 3/2004 | Reid et al. | 424/535 |
| 2006/0040025 | A1 | * | 2/2006 | Souppe | 426/490 |
| 2008/0044544 | A1 | * | 2/2008 | Souppe | 426/580 |
| 2008/0063765 | A1 | * | 3/2008 | Barbano et al. | 426/330.2 |
| 2010/0047428 | A1 | * | 2/2010 | Lejars et al. | 426/580 |
| 2011/0159164 | A1 | * | 6/2011 | Nakata et al. | 426/580 |
| 2011/0189337 | A1 | | 8/2011 | Vembu | |

FOREIGN PATENT DOCUMENTS

| EP | 0786473 | 7/1997 |
|---|---|---|
| EP | 1602284 | 12/2005 |

OTHER PUBLICATIONS

Uenishi et al. Osteoporos. Int. 2007. vol. 18, pp. 385-390.*
Kawakami, H. Bull. Intl. Dairy Feder. 2007. vol. 413, pp. 40-47.*
PCT International Search Report mailed Jun. 4, 2012 for PCT App. No. PCT/US2010/050202.
Kruger, M.C., "The effect of whey acidic protein fractions on bone loss in the ovariectomised rat", British Journal of Nutrition (2005), 93, 244-252.
Lee, J., "Effects of Colostrum Basic Protein from Colostrum Whey Protein: Increases in Osteoblast Proliferation and Bone Metabolism", J Food Sci Nutr, vol. 12, p. 1-6 (2007).
Krissansen, G. "Emerging Health Properties of Whey Proteins and Their Clinical Implications", Journal of the American College of Nutrition, vol. 26, No. 6, 713S-723S (2007).
Mark, A.B., "Milk-derived proteins and minerals alter serum osteocalcin in prepubertal boys after 7 days", Nutrition Research 30 (2010) 558-564.
Armbrecht, H. J., "Stimulation of Intestinal Calcium and Phosphorus Absorption by Carbohydrates," Proteins, Carbohydrates, and Lipids, 237-243, 1990.
Flood, A., "Calcium from Diet and Supplements is Associated With reduced Risk of Colorectal Cancer in a Prospective Cohort of Women," Cancer Epidemiology, Biomarkers & Prevention 2005; 14(1). Jan. 2005, 126-132.
Fratzl, P., "Bone Mineralization in an Osteogenesis Imperfecta Mouse Model Studied by Small-Angle X-ray Scattering," J. Clin. Invest., The American Society for Clinical Investigation, Inc., vol. 97, No. 2, Jan. 1996, 396-402.
Ilich, J. Z., "Nutrition in Bone Health Revisited: A Story Beyond Calcium," Journal of the American College of Nutrition, vol. 19, No. 6, 715-737 (2000).
Kruger, M. C., "The effect of whey acidic protein fractions on bone loss in the ovariectomised rat," British Journal of Nutrition (2005), 93, 244-252.
Madden, A., "Dietary calcium Intake of Diabetics," Ir. J. Fd. Sci. Technol., vol. 8, No. 2, 152, 1990.
Mercier, P. H.J., "Geometrical parameterization of the crystal chemistry of P63/m apatites: comparison with experimental data and ab initio results," Acta Cryst. (2005). B61, 635-655.
Rodriguez-Lorenzo, L. M., "Structural and Chemical Analysis of Well-crystallized Hydroxyfluorapatites," J. Phys. Chem. B 2003, 107, 8316-8320.
Roschger, P., "Alendronate Increases Degree and Uniformity of Mineralization in Coancellous bone and Decreases the Porosity in Cortical Bone of Osteoporotic Women," Elsevier Science Inc., Bone vol. 29, No. 2, Aug. 2001, 185-191.
Scholz-Ahrens, K. E., "Effects of bioactive substances in milk on mineral and trace element metabolism with special reference to casein phosphopeptides," British Journal of Nutrition (2000), 84 Suppl. 1, S147-S153.
Tas, A. C., "Molten Salt Synthesis of Calcium Hydroxyapatite Whiskers," Journal of the American Ceramic Society, 84 No. 2, 295-300 F 2001.

(Continued)

Primary Examiner — Chris R Tate
(74) Attorney, Agent, or Firm — Whyte Hirschboeck Dudek S.C.

(57) ABSTRACT

The present invention is a new method and composition that enhance bone repair, formation, maintenance and slowing of bone resorption. The present invention relates to methods and compositions that enhance collagen formation, tendon health and tendon injury healing, bone maintenance and bone injury healing, and the prevention and treatment of metabolic diseases. The present invention is a part of the therapy to maintain bone health among patients with diabetic bone resorption and others with metabolic disorders. In one embodiment, the composition is a composite of hydroxyapatite and an organic matrix composed of milk pH-dependent serum proteins, i.e., bone morphogenic proteins (BMP), milk serum-derived specific proteins (MSSP), and milk serum derived proteins.

7 Claims, 28 Drawing Sheets

(56) References Cited

OTHER PUBLICATIONS

University of Guelph, Chemistry and Physics (website-printed Jan. 19, 2007), 16 pages.

Vegarud, G. E., "Mineral-binding milk proteins and peptides; occurrence, biochemical and technological characteristics," British Journal of Nutrition (2000), 84 Suppl. 1, S91-S98.

Widdowson, E. M., "Effect of Giving Phosphate Supplements to Breast-Fed Babies on Absorption and Excretion of Calcium, Strontium, Magnesium, and Phosphorus," Original Articles, The Lancet, Dec. 14, 1963, 1250-1251.

Zizak, I., "Characteristics of mineral particles in the human bone/cartilage interface," Journal of Structural Biology 141 (2003), 208-217.

* cited by examiner

COMPOSITIONS AND METHODS FOR THE PREVENTION AND TREATMENT OF METABOLIC DISEASES

CROSS REFERENCE TO RELATED APPLICATIONS

This application is a nonprovisional of application Ser. No. 61/245,505 which was filed on Sep. 24, 2009, the disclosure of which is incorporated by reference herein in its entirety.

FIELD OF THE INVENTION

Bone is an active body system, which tends toward an equilibrium between bone formation (osteoblastic activity) and bone resorption, or loss (osteoclastic activity). Normal bone is composed of 65% mineral matrix, primarily composed of calcium hydroxy apatite and other minerals, the rest comprising organic or protein matrix materials. Ninety percent (90%) is made of collagen Type 1 and the remaining 10% is composed of non-collagenous proteins comprising calcium binding proteins, adhesive proteins and mineralizing proteins consisting of enzymes, cytokines and growth factors. Osteoporosis is a condition where there is a shift toward increased bone resorption, resulting in a net bone loss, making the bone more fragile and prone to breakage.

Osteoporosis, with its precursor condition of bone loss, is a serious healthcare issue that affects 44 million Americans. Many more, including young persons, are at risk of osteoporosis (1-4). Recent research into the biochemistry of bone formation and the suppression of bone resorption has led to the development of new therapies and programs for the prevention and treatment of bone loss and osteoporosis. Milk contains the best-known sources of nutrients for healthy bone growth in young persons and maintenance of bone in the adult populations. In addition to milk-based calcium, milk contains a balanced bio-available mineral profile, bone morphogenic proteins (BMP), milk serum carbohydrates and essential fatty acids for the growth, development and maintenance of bones, teeth and skeletal structures. Milk derived basic proteins (MBP) have been shown to promote bone formation and slow excess bone resorption.

Hydroxyapatite (HAP), particularly calcium hydroxyapatite, is the major constituent of mammalian bone. It is a derivation of apatite class (the most phosphorus-bearing materials) with isomorphous series:

$Ca_{10}(PO_4)_6(Cl, F, OH)_2$: chloro, fluoro and hydroxyapatite.

Various studies in recent years have focused on HAP growth mechanisms from extra-cellular body fluids (human blood plasma).

Proteins, specifically acidic or basic proteins, most likely play an important role in nucleation and growth modification, similar to other bio-mineralization systems such as biogenic $CaCO_3$. It is believed that peptides are instrumental in inhibiting growth of HAP in a particular direction or surface planes (crystal faces). Specifically, the roles of, for example, glutamate ($R-COO^-$) versus phosphorserine ($R-PO_4^{2-}$) amino acid residues is highly controversial and is under extensive research scrutiny.

Milk, specifically domesticated cow milk, is a primary source of the species and nutrients discussed above. Milk provides nourishment and immunological protection for mammalian young and is a source of food, minerals and other nutrients for more mature mammals. Milk is a very complex food containing, in one estimation, over 100,000 molecular species.

BRIEF SUMMARY OF THE INVENTION

Compounds and formulations of this invention are a milk-based therapeutic formulation, which comprise milk serum-specific proteins which are basic or acidic in nature, bone morphogenic proteins and other factors capable of promoting bone formation and inhibiting bone resorption. The examples and disclosure herein demonstrate the efficacy of this invention in slowing bone resorption and provide evidence inferring compounds of this invention actually stimulate bone formation.

Briefly, in one aspect, the present invention is a new product for collagen-formation, collagen repair, bone repair, bone formation, maintenance, and regeneration. This invention is a nano-composite of hydroxyapatite nano-fibers and an organic matrix composed of milk pH-dependent serum proteins, i.e., bone morphogenic proteins (BMP), milk serum-derived specific proteins (MSSP), milk serum derived proteins, both basic and acidic in nature with various positive and negative charges. For purposes of this invention, "milk serum proteins" are defined as milk minus naturally occurring casein or casein-free milk. Representative serum proteins present in this invention include but are not limited to β-lactoglobulin (formerly called lactalbumin), α-lactoglobulin (formerly called lactalbumin), Lactoferrin, Lactoperoxidase, IgG, IgM ('m' chain), secretory piece, (secretory piece is a glycoprotein often found associated with IgA), α-casein, bovine serum albumin, IgA ('a' chain) or IgD ('d' chain), glycoproteins, casein phosphopeptides, lipoprotein A1, retinol-binding protein, osteopontin and its fragments and other minor proteins such as growth Factors and pre-albumin. It exists as hydroxyapatite in natural form and therefore is hexagonal in shape.

Applicant has developed, and discloses herein, a new milk-based therapeutic formulation containing for example, the patented material, of U.S. Pat. No. 5,639,501, sometimes referred to herein as "DariCal", containing a unique combination of two forms of high quality milk calcium—calcium phosphate and calcium lactate. The DariCal material includes minerals with high bio-availability, Proteins, carbohydrates and fatty acids. A compound of the current invention, herein sometime referred to as "Hexamenicol" for identification purposes in addition to the above, contains milk-serum-derived specific proteins of acidic and basic in nature (MSSP) and bone morphogenic proteins (BMP) such as alpha-lactalbumin, beta-lactglobulin, immuno-gammaglobulin, growth factors, Lactoferrin, Lactoperoxidase and other valuable peptides and amino acids. These proteins, peptides and amino acids have been shown to stimulate bone growth and slow down bone resorption. The Hexamenicol material has approximately the same mineral profile (proportions and content) as bone (Table 1) and provides these organic precursors and inorganic components necessary for the manufacture and maintenance of bone.

TABLE 1

Hexamenicol ™ Mineral Analysis Compared with Bone

| Element | Hexamenicol | Bone |
|---|---|---|
| Calcium (Ca) | 26.0% | 25.0% |
| Phosphorus (P) | 15.5% | 12.0% |
| Magnesium (Mg) | 1.5% | 0.37% |

TABLE 1-continued

Hexamenicol ™ Mineral Analysis Compared with Bone

| Element | Hexamenicol | Bone |
| --- | --- | --- |
| Potassium (K) | 0.5% | 0.5% |
| Zinc (Zn) | 15.0 ppm | 9.0 ppm |
| Iron (Fe) | 26.0 ppm | 21.0 ppm |
| Manganese (Mn) | 1.5 ppm | 1.2 ppm |
| Copper (Cu) | 3.2 ppm | 0.5 ppm |

In addition to the mineral analysis the other materials present in the compound are: the total protein content in Kjeldahl analysis may range from 2.0% to 10% depending on the need to maintain the protein content and type of proteins desired for a particular function. The product may also contain fatty acid content between 0.04% to 0.06% with a fatty acid profiles of cupric acid, caproic acid, Linoleic acid and oleic acid groups. The product may also contain total carbohydrate (CHO) content in the range of 4 to 9% composed of lactose, glucose, maltose and fructose.

BRIEF DESCRIPTION OF THE FIGURES

The invention will now be illustrated by the attached Figures, Detailed Description and appended Claims, all of which should be considered exemplary and not limiting of the present invention and in which:

DETAILED DESCRIPTION OF THE INVENTION

Figure 1:
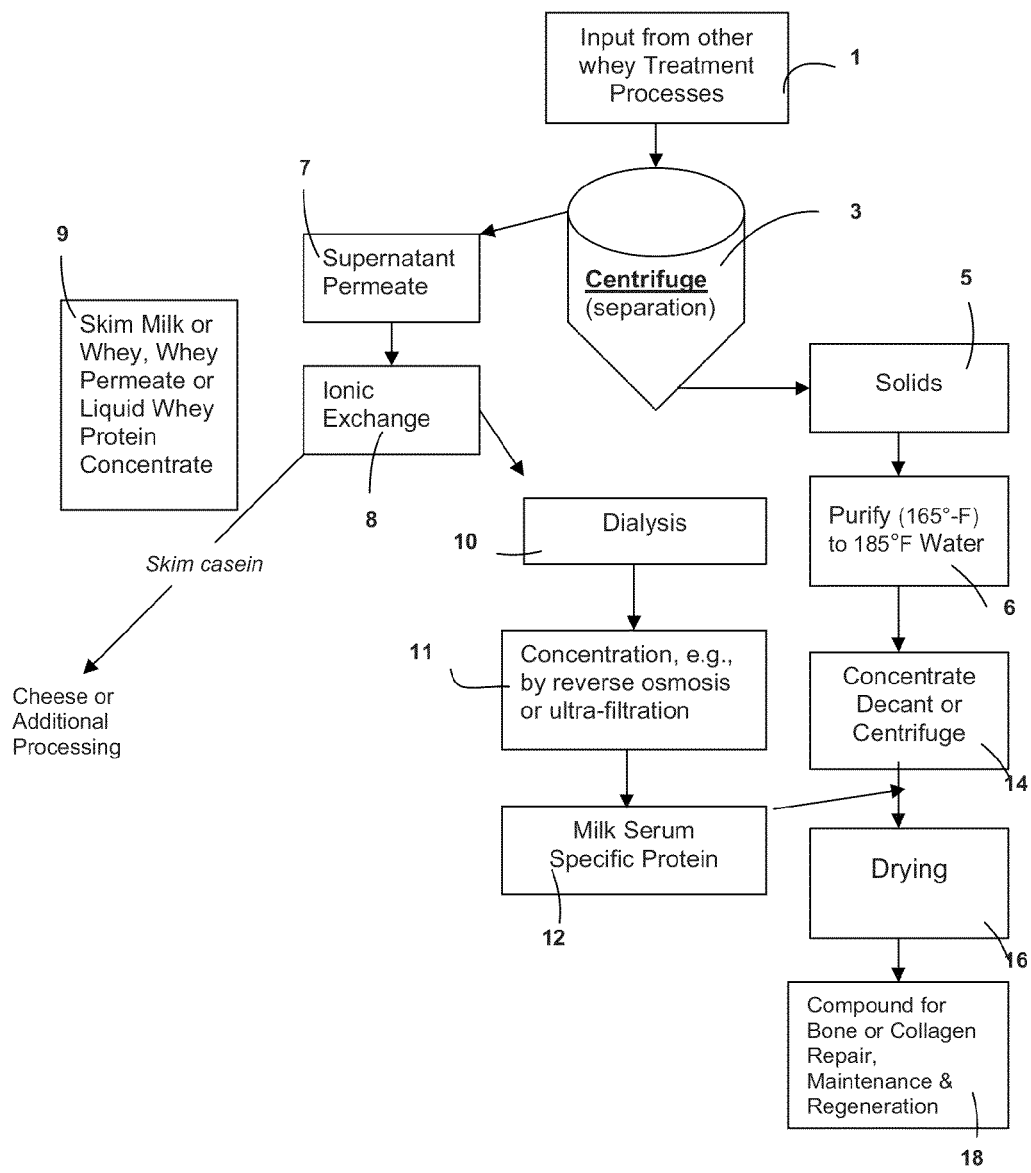
FIG. 1 is a flowchart showing one embodiment of method used in this invention.

Referring now to FIG. 1 there is shown a flow chart of a process of the present invention. As is shown, at box 1 there is a raw material input of treated whey from some "other" whey treatment process meaning a treatment process other than one of this invention. An exemplary whey treatment process, as was noted above, is described in U.S. Pat. No. 5,639,501 to Rajan Vembu et al., the teachings of which are incorporated by reference herein. As is shown in box 1, the previously treated whey is decanted into, for example, centrifuge 3 for separation of solids (to box 5) from liquids (to box 7). Other processes for separation of whey solids from liquids, i.e., other than centrifugation, may be used and are within the contemplation of this invention.

The liquid permeate or supernatant generated in the separation step at 3 is transferred in box 7 comprises water, lactose, sodium-based minerals, and soluble polypeptides. As shown, the supernatant of box 7 is exposed to a chromatographic ion exchange process in box 8. Optionally and sequentially, and not normally concurrently, additional skim milk, whey, or whey permeate, whey serum protein (shown in box 9 as being added skim milk, whey, whey permeate, or liquid whey protein concentrate) is also subjected to ionic exchange. The ionic exchange material used in box 8 is positively (+) charged, thereby causing negatively (−) charged proteins to be separated from the liquid by being retained by the column. Positively charged proteins, regardless of source (i.e., regardless of whether they originated from separation at 3 or were added as shown in box 9) pass through the positively charged ion exchange column without being retained and proceed to a dialysis step, as necessary as shown in box 10. The dialysis step as shown in box 10 removes substantially all sodium-based milk minerals and sodium chloride, generating an effluent stream of substantially pure negatively charged milk serum protein.

Parallel to the process steps shown in boxes 3,7,8,10, and 12 the solids separated at 3 are transferred (box 5) and purified 6, e.g., by diluting the solids in water and heating the solution to a temperature of at least about 165° F. to 185° F. for a time period of not more than about 1 hour. The solids purified in this step substantially comprise divalent milk minerals, preferably of the alkaline earth family e.g., $Ca^{2+}$ and $Mg^{2+}$ but including other divalent species such as $Cu^{2+}$, and $Mn^{2+}$. The divalent milk minerals purified as shown in box 6 are concentrated in box 14 e.g., by centrifugation. The milk serum proteins originating from box 12 and the divalent milk minerals originating from box 14 then are combined (not shown by a separate box) and dried as shown in box 16. The crystalline morphology, x-ray diffraction characteristics, elemental composition, and surface area of this milk serum protein/mineral composite material 18 are described in detail below.

Figure 2:
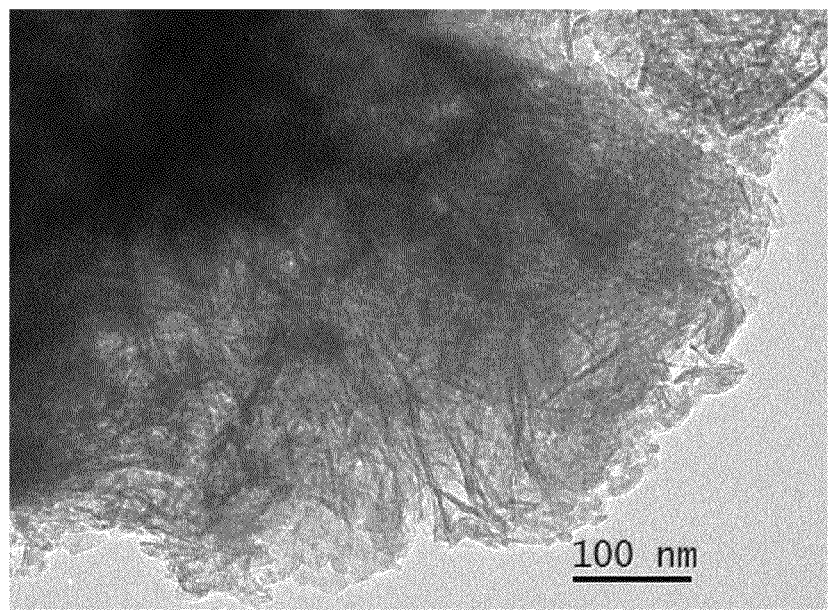
FIG. 2 is a TEM image showing aggregates of hydroxyapatite nano-fibers of the new invention.
Figure 3:
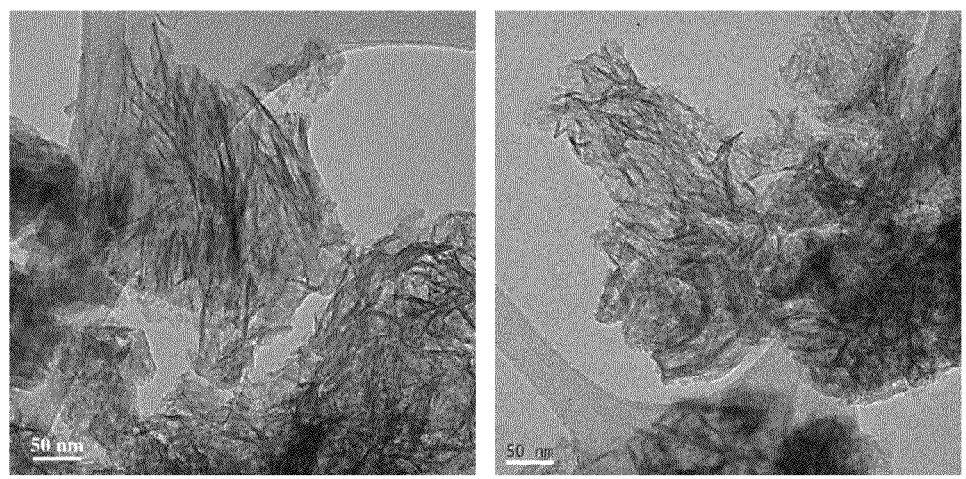
FIG. 3 are TEM images showing bundles and aggregates of hydroxyapatite nano-fibers of the new compound. The amorphous organic "matrix" can be clearly seen along the thin edge areas. Both images were recorded under same magnification.
Figure 4:
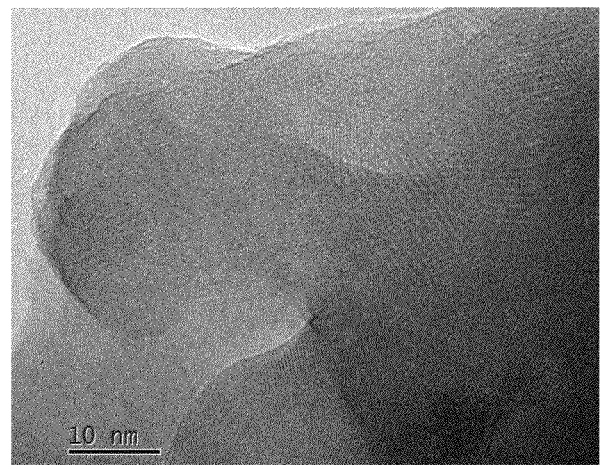
FIG. 4 is a high-resolution TEM image showing lattice fringes (crystalline nature) of the nano-fibers crisscrossing like a woven cloth (overlap of many crystals) as compared to calcium carbonate and calcium hydroxyapatite, which run in a single direction. As shown the lattices-overlap and cross to form layer upon layer of crossing fibrils.
Figure 5:
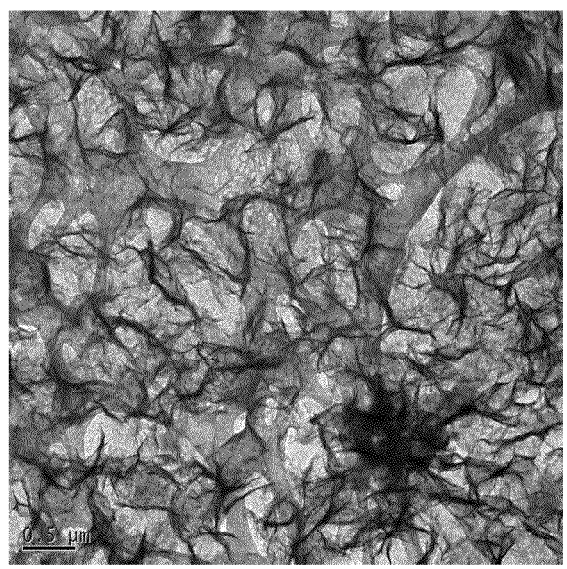
FIG. 5 is a TEM image of the new compound showing the amorphous CI-bearing Ca-phosphate aggregates in solution at pH=2.0.
Figure 6:
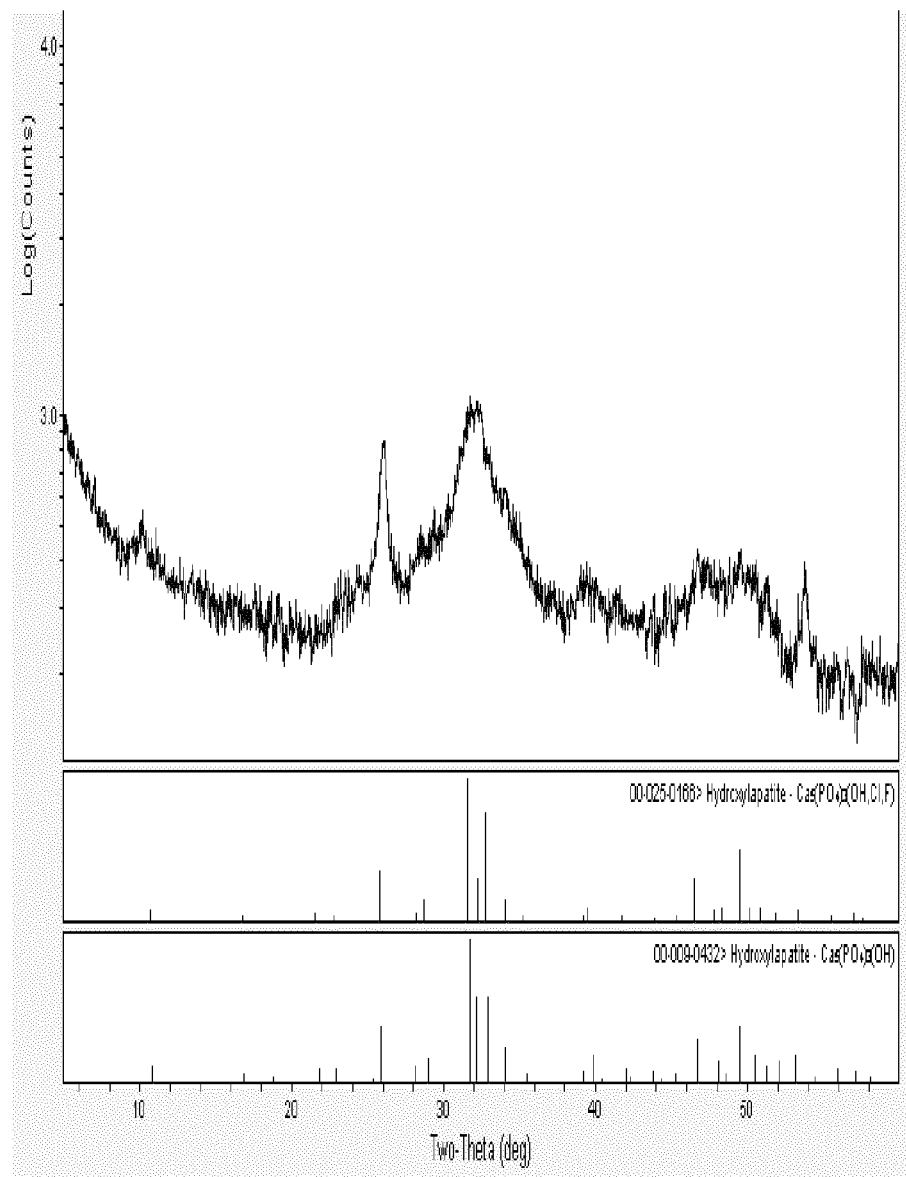
FIG. 6 is an XRD pattern for the new compound sample.
Figure 7:
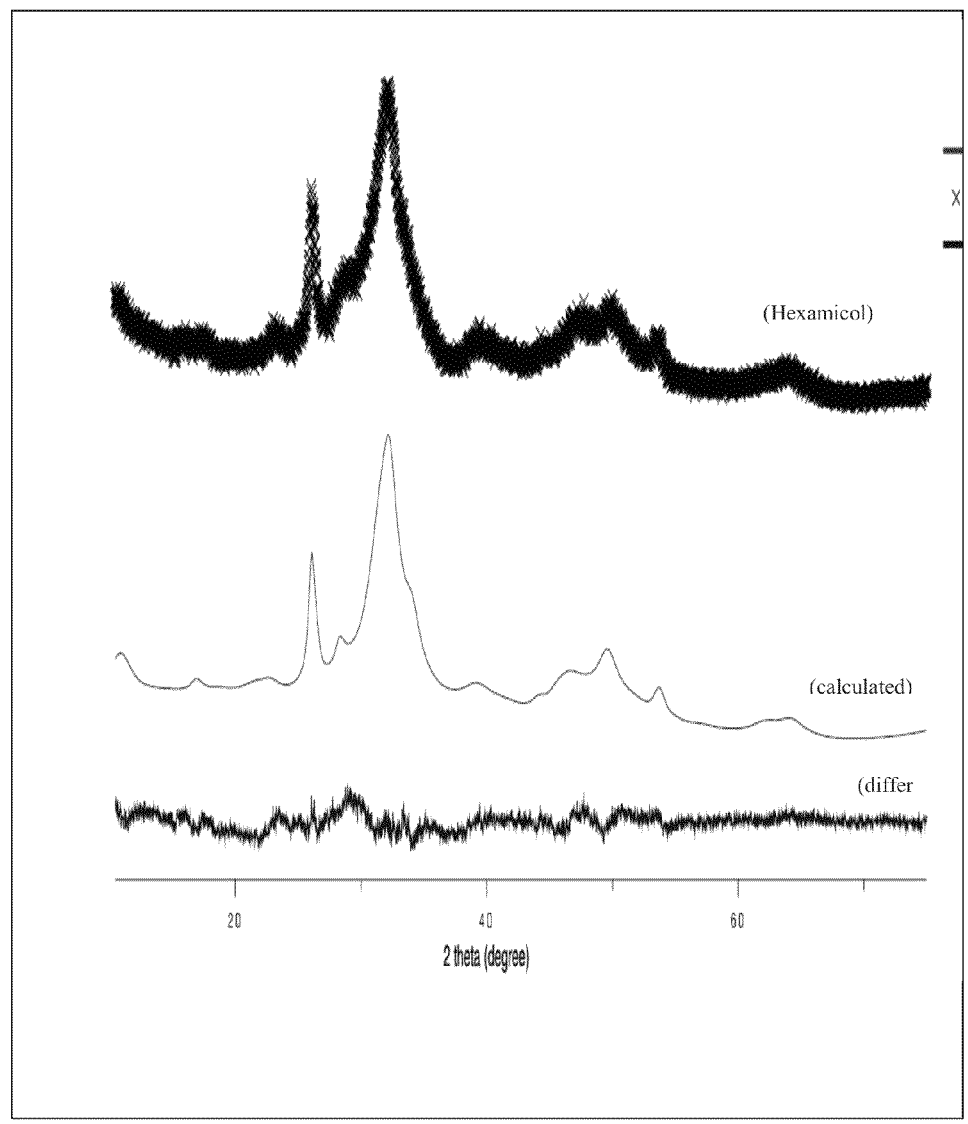
FIG. 7 is an X-ray diffraction pattern and simulated pattern (best fit) for the new compound apatite.
Figure 8:
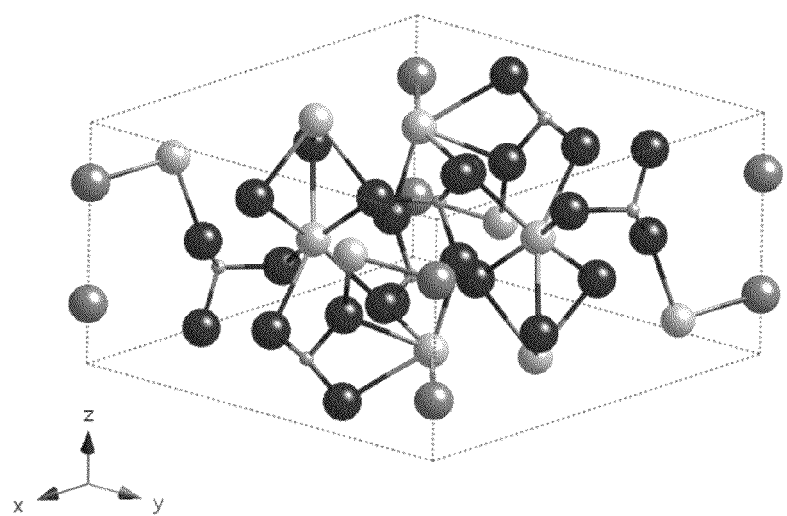
FIG. 8 is a 3-D model showing atoms within the unit cell. Red: oxygen; Blue: OH (basically shows O of OH); Blue/green: Ca; Purple-brown: P.
Figure 9:
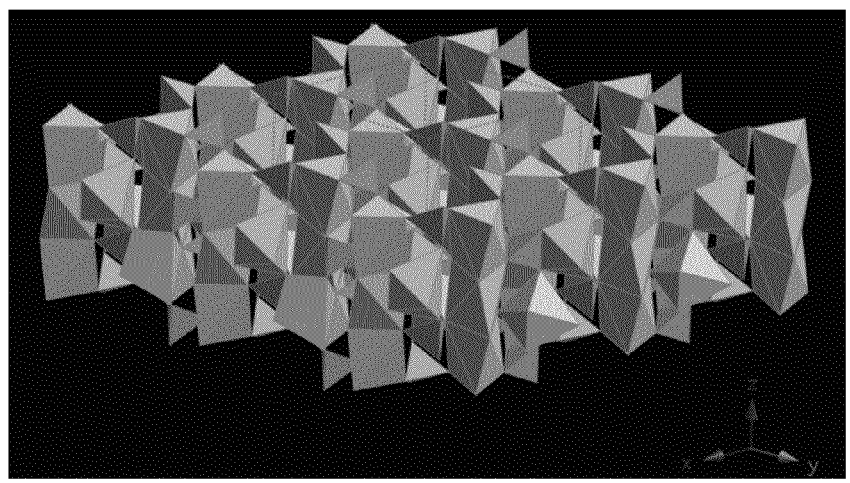
FIG. 9 is a 3-D polyhedral model of apatite structure. P are in tetrahedra (Purple-brown color). Ca are in poly hedra with coordination numbers of 7 and 9 respectively.
Figure 10:
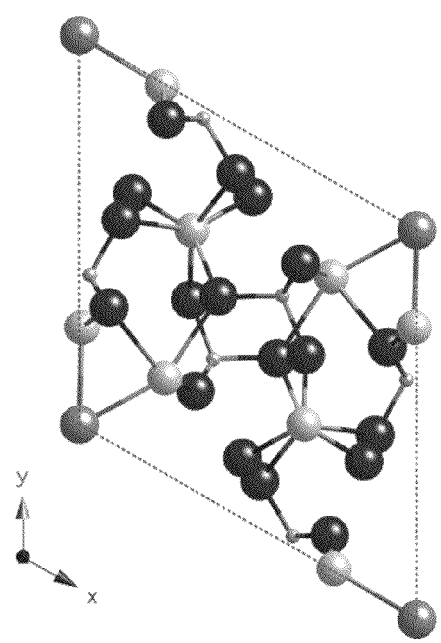
FIG. 10 is a projection of the atoms within a ½ unit cell along c-axis (or on x-y plane)
Figure 11:
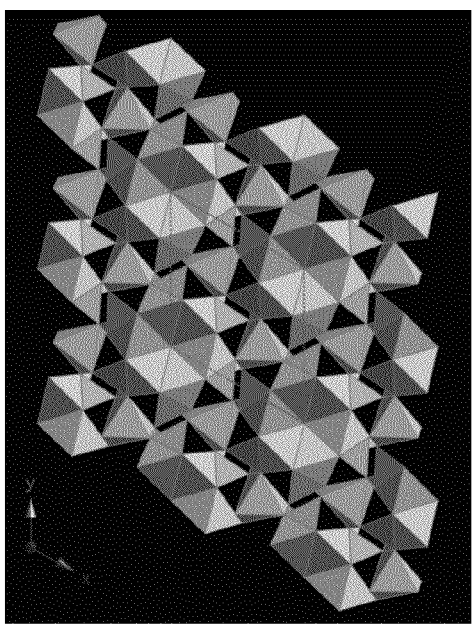
FIG. 11 is a polyhedral model of the apatite structure projected along c-axis (or, on x-y plane). P are in tetrahedra (light brown color). Ca are in polyhedra with coordination numbers of 7 and 9 respectively.
Figure 12:
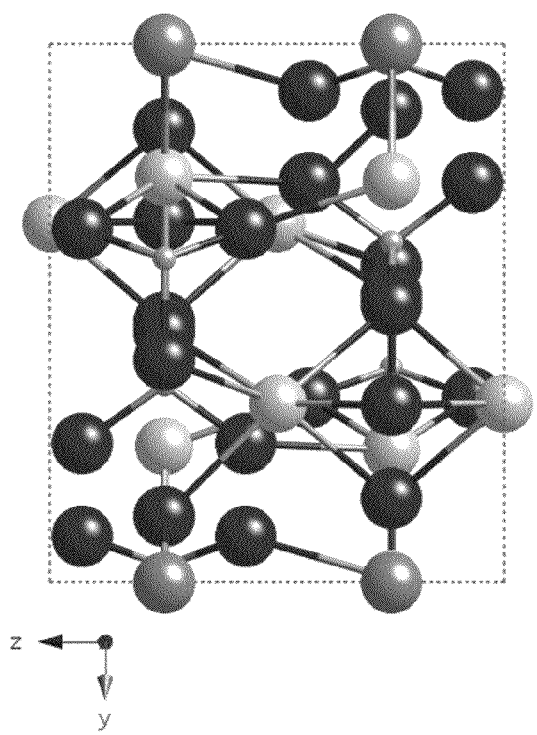
FIG. 12 is a projection of the atoms within unit cell along [100] direction (or on y-z-plane)
Figure 13:
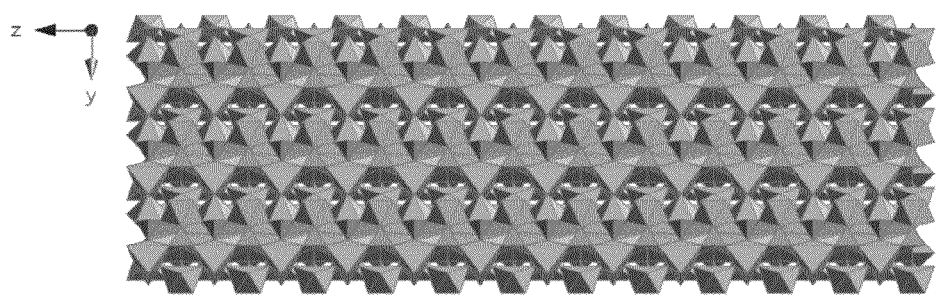
FIG. 13 is a polyhedral model schematically showing an apatite nano-fiber of the invention.
Figure 14:
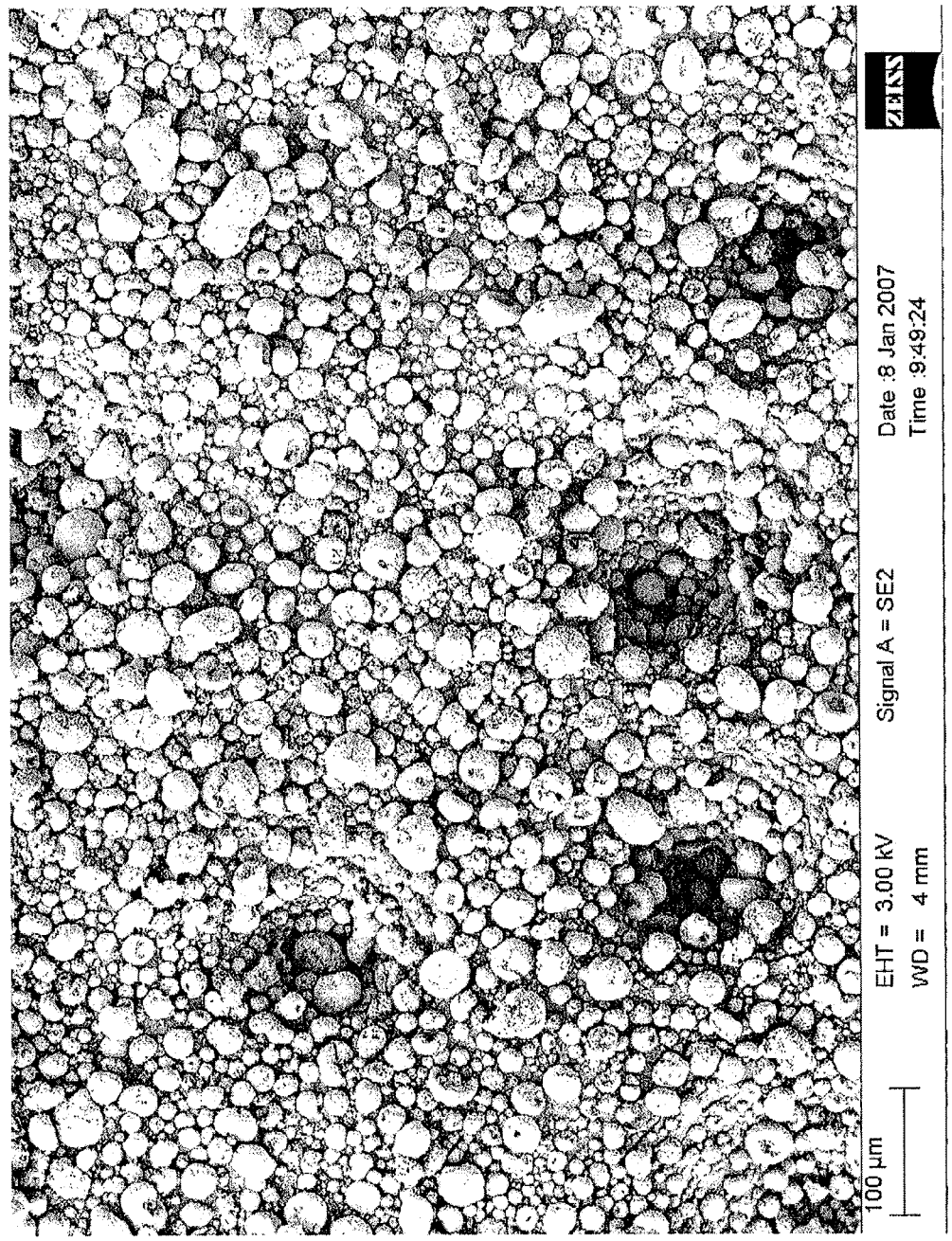
FIG. 14 is a photomicrograph of a product of this invention such as it appears after drying step (e.g., spray drying) 16 in FIG. 1 (scale is shown).
Figure 15:
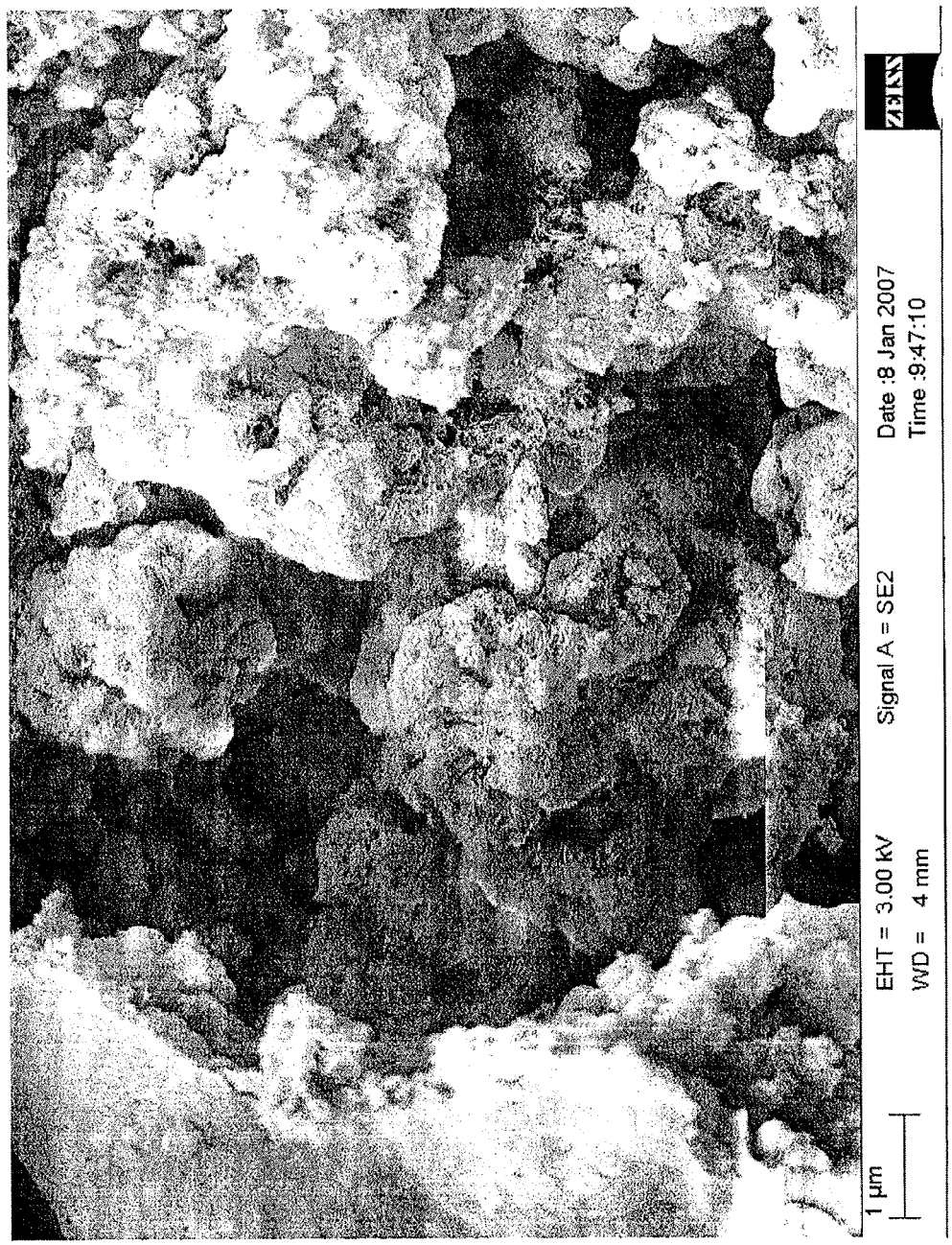
FIG. 15 is a photomicrograph of the material of FIG. 14 at higher magnification (scale is shown).
Figure 16:
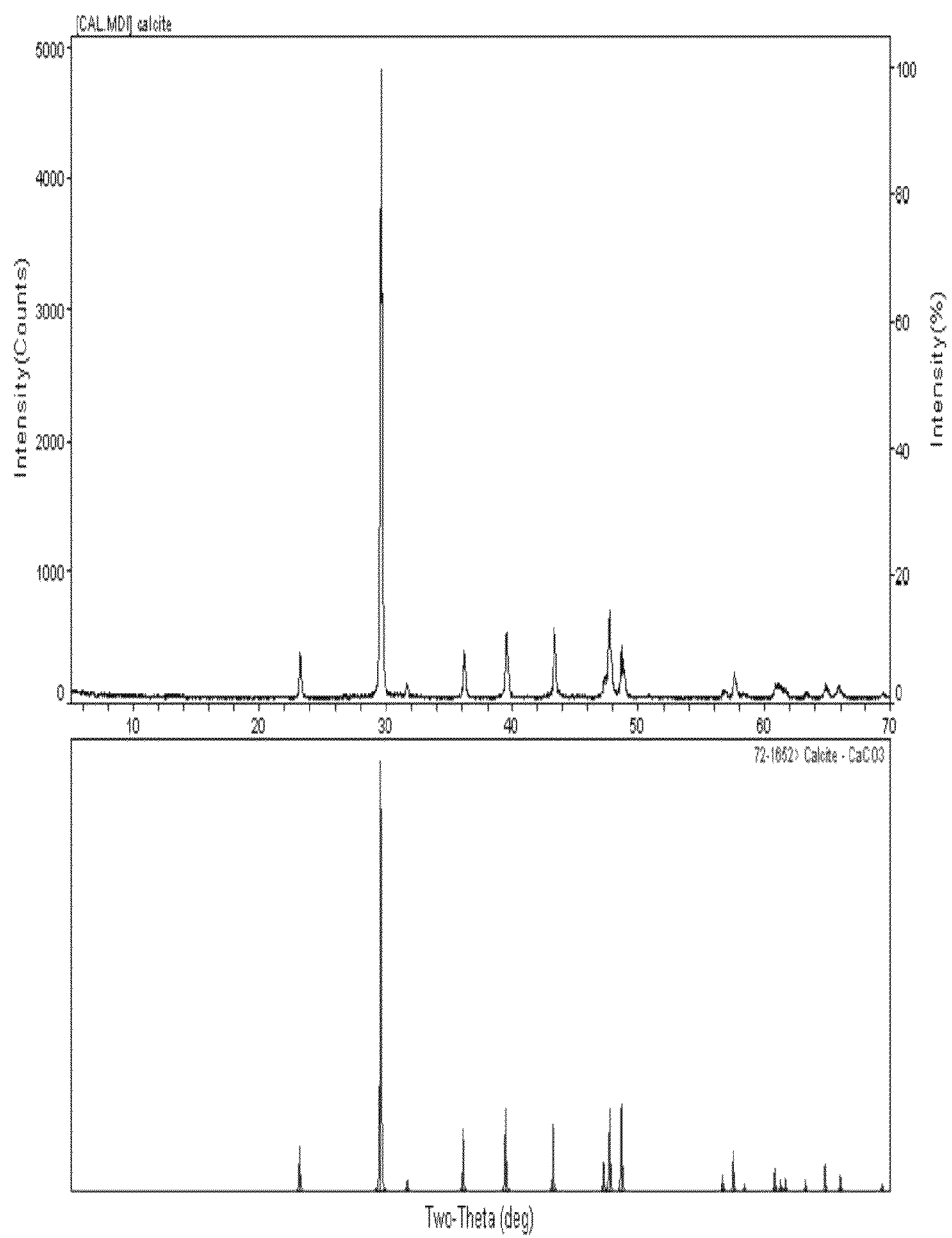
FIG. 16 is a comparison of current therapies, the XRD pattern commercial Calcium Carbonate, USP Pharma grade supplier Generichem Corp. commonly used in the manufacture of calcium tablets. Surface Area: generally about 2.7 $m^2/g$. XRD patterns from the sample (upper plot) and peaks from reference file in data base (lower plot). The diffraction pattern matches calcite very well. This FIG. is included for purposes of comparison.
Figure 17:
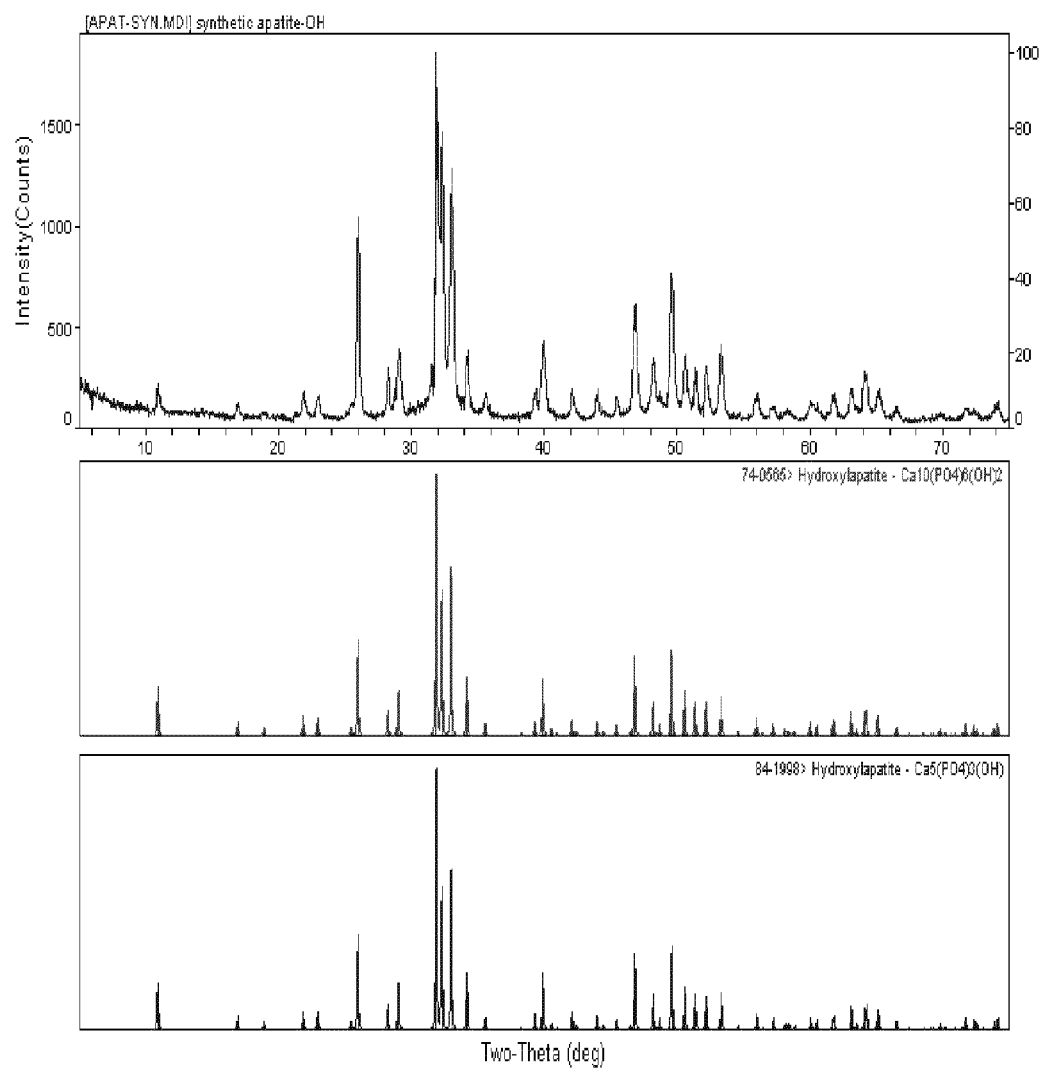
FIG. 17 is the XRD pattern of synthetic calcium hydroxyapatite from Aldrich chemicals, St. Louis, Mo. Surface Area: 29.6 $m^2/g$. XRD patterns from the sample (top plot) and peaks from reference files in data base (middle and lower plots). The diffraction pattern matches hydroxyapatite very well. Relatively strong intensities and sharp peaks indicate large apatite crystals.

Transmission electron microscopic (TEM) images show aggregates and bundles of the hydroxyapatite nano-fibers with non-crystalline organics among them (FIGS. 2, 3). The average diameter of the apatite is about 5 nm. The length of the nano-fibers is about tens to several hundreds of nanometers. The elongation direction is c-axis of the apatite crystal. Non-crystalline foil-like organic materials are "matrix" of the samples. The apatite nano-fibers are "glued" together by the organic materials. The apatite nano-fibers are very reactive and unstable under electron beam (with respect to normal synthetic apatite crystals).

Description: A compound of the invention exists, in part, as hydroxyapatite in its natural form and therefore is hexagonal in shape.

A compound of this invention promotes bone repair, formation, maintenance, regeneration and collagen formation. The present invention relates to methods and compositions that enhance collagen formation, tendon health and healing, bone health and healing, and maintaining and aiding in diabetic bone resorption. The present invention is useful in the treatment of metabolic disorders. It is a nano-composite of hydroxyapatite nano-fibers and organic matrix composed of milk serum specific proteins of basic and acidic in nature with various positive and negative charges. The proteins are pH dependent and include but are not limited to α-lacto globulin (formerly called lactalbumin), β-lacto globulin (formerly called lactalbumin), Lactoferrin, Lactoperoxidase, IgG, IgM (m chain), secretory piece*, (*secretory piece is a glycoprotein often found associated with IgA), α-(alpha)casein, bovine serum albumin, IgA (a chain) or IgD (d chain), glycoproteins, casein phosphopeptides, lipoproteinA1, retinol-binding protein and other minor proteins such as bovine growth hormone and pre-albumin.

Transmission electron microscopic (TEM) images of a material of this invention show aggregates and bundles of the hydroxyapatite nano-fibers with non-crystalline organics among them (See, e.g., FIGS. 2, 3). The average diameter of the apatite is about 5 nm. The length of the nano-fibers is about tens to several hundreds of nanometers. The elongation direction is c-axis of the apatite crystal. Non-crystalline foil-like organic materials are "matrix" of the samples. The apatite nano-fibers are "glued" together by the organic materials. The apatite nano-fibers are very reactive and tend to be unstable under electron beam exposure with respect to normal synthetic apatite crystals.

While not wishing to be bound by any theories Markus Buehler of the Massachusetts Institute of Technology has opined that unlike conventional building materials, which tend to be homogenous, bone is heterogeneous living tissue with cells constantly changing. Scientists classify bone's basic structure into a hierarchy of seven levels of increasing size. Level 1 bone consists of chalk-like hydroxyapatite and collagen fibrils, which are strands of tough proteins. Level 2 comprises a merging of these two into mineralized collagen fibrils that are much stronger than the collagen fibrils alone. The hierarchical structure continues in this way through increasingly larger combinations of the two basic materials until level 7, or whole bone comprising generally of 35% protein or organic matrix and 65% of mineral matrix.

At the molecular level, mineralized collagen fibrils are made up of strings of alternating collagen molecules and consistently sized hydroxyapatite crystals. These strings are "stacked" together but staggered so that crystals resemble stairs. Weak bonds form between the crystals and molecules in and between strings.

Pressing the fabric-like fibrils breaks some weak bonds between the collagen molecules and crystals, creating small gaps or stretched areas in the fibrils. Stretching spreads the pressure over a broader area, and in effect, protects other, stronger bonds within the collagen molecule, which might break outright if the pressure was focused on them. Stretching also lets the crystals move in response to the force, rather than shatter, which would be the likely response of a larger crystal. It is theorized that this ability to absorb energy may reduce bone breakage, e.g., in a fall.

Buehler observed that bone has a unique ability to tolerate gaps in the stretched fibril fabric. These gaps are of the same magnitude—several hundred micrometers—as the basic multicellular units associated with bone's remodeling. The units are a combination of cells that work together like a small boring worm that eats away old bone at one end and replaces it at the other, forming small crack-like cavities in between as it moves through the tissue.

Thus, the mechanism responsible for bone's strength at the molecular scale also explains how bone can remain strong, even though it contains the many tiny cracks required for its renewal. Bone creates strength by taking advantage of the gaps, which are made possible by the material's hierarchical structure. Nov. 1, 2007, "How Bone is Built May Lead to New Materials," http://medicaldesign.com/materials/bone. Visited Mar. 31, 2009.

Surface area of the new compound is 207.5 $m^2/g$. It is very high compared to those of synthetic hydroxyapatite (from Aldrich Chemicals, St. Louis, Mo.) (29.6 $m^2/g$) and a commercial calcium Carbonate product (Pharma grade powder from Generichem Corporation, NJ used for calcium supplement tablet making) (2.7 $m^2/g$). It can be inferred that the product of this invention is very reactive considering its large reactive surface. Preliminary studies show a compound of this invention to be about 76 times more reactive than calcium carbonate, a widely used supplement in the industry.

Chemical Reaction in pH 2 Solutions:

The solution was adjusted by using HCl (0.1M) acid. The amount of 0.05 g of the sample can be dissolved completely in the 100 ml pH2 solution. The final solution is clear with pH value of 3.5. Adding 0.15 g of the sample into the 100 ml pH 2 solution, the final solution is not clear, is opaque and it looks like suspension that contains colloid-like particles. The solution of the pH rises to 4.7. The particles in the suspension were analyzed using transmission electron microscope. The particles are amorphous Cl-bearing Ca-phosphate. It is proposed that the original hydroxyapatite nano-fibers were dissolved and the amorphous Cl-bearing phosphate can precipitate from the Cl-bearing solution.

Dissolution Kinetics Based on One Set of Dissolution Experiments:

Experimental condition: 0.05 g of Hexamenicol added into 20 ml pH2 solutions, and reacted with compound of the invention at room temperature for 0.5 hr, 1 hr, 2 hr, and 3 hr. The reaction products were centrifuged right after they reached the set up reaction time in order to separate solution and remaining solids. The remaining solids were dried and weighted carefully in order to evaluate the mineral electrolytes, which are charged and thereby combine with positively and negatively charged proteins. For example, $Ca^{2+}$ molecules have a positive charge, and therefore interact and attract negatively charged molecules.

Chemical Formula Based on Chemical Analysis:

The chemical formula is based on the provided results and normalized to 3 P. $(Ca_{4.963}, Mg_{0.0365}, Sr_{0.0005})(PO_4)_3(OH_{0.82}, Cl_{0.15}, F_{0.03})$. Generally, $Ca_5(PO_4)_3.OH$ with randomly placed Na, K. The molecular weight is: 506.34 (g per formula).

It is a hydroxyapatite. Na and K are in soluble salt forms. It is also possible that trace amount of Mg in soluble form.

The calculated density of the apatite based on measure unit cell parameters and obtained chemical formula is 3.15 g/cm$^3$. In general, it is slightly lower than the calculated value of macroscopic hydroxyapatite apatite crystals.

X-Ray Diffraction Analysis:

X-ray powder diffraction pattern shows that the crystalline phase in bulk powder sample is a nano-crystalline apatite (hydroxyapatite). All the diffraction peaks are very broad except for a strong and relatively sharp 002 diffraction peak (d=3.416 A). The shapes of the diffraction peaks indicate that the hydroxyapatite crystals are nano-fibrous crystals with elongation direction along c-axis.

Unit Cell Refinement:

The unit cell parameters of the New Compound apatite were calculated based on a whole pattern refinement method (Rietveld method) based on a published average structure of hydroxyapatite. The results show that a-dimension and b-dimension of the unit cell are slightly larger than that of standard hydroxyapatite. However, its c-dimension is slightly smaller than that of standard hydroxyapatite. It is proposed that nano-fiber affects structural relaxation of the apatite structure, especially atoms on surface and nearby surface. It is expected atomic coordinates for the New Compound apatite structure may be slightly different from the reference structure. However, it is impractical to refine the coordinates based on diffraction pattern with very broad diffraction peaks.

TABLE 2

| Fractional Co-ordinates of the atoms | | | | |
|---|---|---|---|---|
| Atom | x | y | z | occupancy |
| Ca-1 | 0.33333 | 0.66667 | 0.0015 | 1.00000 |
| P | 0.3987 | 0.3685 | 0.2500 | 1.00000 |
| OH | 0.00000 | 0.00000 | 0.1950 | 0.50000 |

TABLE 2-continued

| Fractional Co-ordinates of the atoms | | | | |
|---|---|---|---|---|
| Atom | x | y | z | occupancy |
| O-1 | 0.3284 | 0.4848 | 0.25000 | 1.00000 |
| O-2 | 0.5873 | 0.4651 | 0.25000 | 1.00000 |
| O-3 | 0.3437 | 0.2579 | 0.0702 | 1.00000 |

Unit Cell Parameters for the Apatite Compound of this Invention:
a=b=9.500 Å
c=6.821 Å
alpha=90.00°
beta=90.00°
gamma=120.00°
Symmetry: space group $P6_3/m$.

Unit Cell Parameters of a Reference Hydroxyapatite:
a=b=9.416 Å
c=6.875 Å
alpha=90.00°
beta=90.00°
gamma=120.00°
Symmetry: space group $P6_3/m$.

Photomicrographs of this material are shown in the Figures.

SUBJECTS AND METHODS

Generally

Subjects.

Participants were menopausal and postmenopausal women recruited from the population at large in the Madison, Wis. area who were otherwise healthy, not taking any diet supplements and living normal lives. Seventeen women initially signed the consent forms for the study but four were disqualified for non-compliance of the protocol. Thirteen women with ages ranging from forty to seventy-one completed the twelve-week study. The study protocol complied with HIPAA regulations.

Protocol.

After enrollment, each participant was given a urine NTx assay kit with instructions to collect the second void of morning urine sample (pre-treatment) and mail the sample with the return overnight mail to the central testing laboratory (Madison Pharmacy Associates, Madison, Wis.) to establish baseline NTx readings. Participants were notified of their initial readings. Normal NTx readings are below thirty-eight nMBCE, an elevated NTx is between forty to sixty nMBCE and a high NTx is above sixty nMBCE. An elevated NTx is indicative of osteopenia while a high NTx is inferred as osteoporosis in correlating to low BMD and bone loss. Selected participants, with NTx readings higher than thirty eight were mailed Hexamenicol compound in powder form individually packaged in two gram packets for a twelve week supply along with use instructions, daily intake recording calendars, second test NTx kits and other necessary contact information. Participants were required to consume two grams of Hexamenicol powder (500 mg calcium equivalent) two times daily, totaling one thousand mgs of calcium equivalent, two times daily, in the morning and one-half hour before bed-time. Participants had unlimited access to information with study monitors. Participants were contacted every week to verify that they were in compliance with the study protocols, maintaining expected records and assessments were made about how well the product was being tolerated. After twelve weeks of Hexamenicol intake, the participants who were verified to have been in compliance with the protocol were requested to send a second urine sample (post-treatment) by overnight mail.

Urine NTx (a Bone Resorption Marker)

Urine NTx is a method for examining cross-linked N-Teleopeptides of type-I collagen (NTx) that the body excretes in urine when bones are broken down (21, 22). An increased rate of NTx excretion indicates a higher rate of osteoclast activity and bone destruction. Unlike bone mineral density (BMD) measurements, which typically detect changes in bone density over years (23), NTx is able to detect changes in bone metabolism in weeks or months (24). Two possible applications of NTx are to (a) predict bone loss in Peri- and post-menopausal women and to (b) monitor the skeletal response to treatment. While NTx testing does not directly determine osteoporosis, it does determine the likelihood of decreasing bone density, as measured by conventional bone mass measurements. The higher the rate of bone resorption as measured by NTx, the greater the rate of bone loss (22,25). Elevated levels of bone resorption (NTx) markers found in urine are associated with higher rates of bone loss in postmenopausal women (26,27).

Bone resorption markers may also play a role in evaluating the effects of therapy (28). Current osteoporosis treatments act to decrease bone resorption, which is detectable by changes in NTx studies (21). Using markers, the efficacy of treatment may be determined in a matter of months. These shortened timelines for treatment increase feedback response by comparison to changes in bone density that may not be detected for one or two years. Experts suggest that demonstrating early evidence that the osteoporosis regimen may be working can reinforce a patient's desire to continue therapy, enhancing compliance with treatment. Many specialists treating osteoporotic patients use bone resorptive markers in assessing the role of high bone turnover in pathogenesis and prognosis, as well as assessing the response to antiresorptive drugs. Failure to detect a decrease in bone markers could indicate a lack of compliance or efficacy of antiresorptive drug therapy.

DEMOGRAPHICS

TABLE 2a

Demographics of Subjects
n = 13

| | |
|---|---|
| Total number of subjects | 13 |
| Number of pre-menopausal subjects | 3 |
| Number of postmenopausal subjects | 10 |
| Average age of subjects | 58 years |
| Average pre-treatment NTx of all subjects | 49.76nMBCE |
| Average pre-treatment NTx of pre-menopausal subjects | 44.33nMBCE |
| Average pre-treatment NTx of postmenopausal subjects | 51.40nMBCE |

Status of Subjects.

During the twelve-week study period, none of the subjects reported bloating, diarrhea, heartburn, allergy symptoms or adverse reactions from the use of the Hexamenicol™ powder. They all maintained their normal health with routine living. None reported to face adverse conditions in life, none of the subjects were involved or reported to have been in any accident, no allergies of any kind or any treatment for any diagnosis of diseases.

TABLE 3

NTx reading AND Table 3a: Graphs

| Participant Change | Age (years) | Baseline (nMBCE) | Final (nMBCE) | % (nMBCE) |
|---|---|---|---|---|
| 1. | 40 | 43 | 37 | −13.95 |
| 2. | 44 | 46 | 38 | −17.39 |
| 3. | 47 | 44 | 38 | −13.63 |
| 4. | 52 | 45 | 38 | −15.55 |
| 5. | 57 | 43 | 33 | −23.25 |
| 6. | 58 | 45 | 37 | −17.77 |
| 7. | 59 | 47 | 38 | −19.14 |
| 8. | 61 | 44 | 37 | −15.90 |
| 9. | 62 | 46 | 38 | −17.39 |
| 10. | 64 | 50 | 38 | −24.00 |
| 11. | 69 | 60 | 38 | −36.66 |
| 12. | 70 | 61 | 38 | −37.70 |
| 13. | 71 | 73 | 38 | −47.94 |

It is believed that compositions of this invention will be found useful in the following applications: prophylactic (i.e., prevention) and therapeutic (i.e., mitigation) inhibition of types of cancer especially colorectal and breast muscle, tendon building and repair, Type II diabetes; and osteoporosis; All mammalian applications e.g., veterinary, are intended. For example, a material of the present invention is believed to be applicable to the inhibition of loss, bone mass building, healing of bone fractures, and restriction or enhancement (as appropriate) of bone mass density changes. For example a compound of this invention may be used to treat bone fractures and to build bone mass in veterinary applications. For example, dogs have specific applications such as fracture healing and bone mass strengthening or enhancement. Hip dysplasia in dogs is also thought to be treatable i.e., to inhibit the onset or to cause the dysplasia to be reduced or healed using the present compound. The current invention compound, Hexaminacol™ because of its large surface area of 207.5 m2/g is believed to be ideally usable as a carrier for medicines or agents, in the manufacture of tablets, capsules and to deliver in a powder form both in bulk and in smaller delivery doses.

Example 1

The focus of this study is to use computational techniques to determine at the atomic level, the mode of interaction between the HAP and protein/peptide/amino acid factors and milk proteins and to determine whether glutamate or phosphoserine residues are preferred in controlling HAP nucleation and crystal growth.

Classical molecular mechanics/molecular dynamics (MM/MD) technique implemented in FORCITE (Accelrys™) code was used. The MM calculation provides single point energies and geometry optimizations for both molecules and periodic systems.

MD simulations were performed for the NVT ensemble at 300 and 500K for 5 ps with a 1 fs time-step for BSP in solution. For periodic systems, quench dynamics at 350 K for 5 ps with 1 fs time-step were used to give preferential adsorption sites on the surface before geometry optimizations.

Reliability of surface energies and adsorption energies in classical MM simulation relies on the accuracy of potentials. We chose the Universal Force Field (UFF) potentials that were derived for organometallics, hence, should handle our systems fairly accurately.

Example 2

Classical molecular modeling techniques were used to examine the mode of interaction between specific crystal faces of HAP or aqueous $Ca^{2+}$ and $HPO_4^{2-}$ ions and an acidic peptide containing glutamate (R—COO$^-$) and protonated phosphoserine (R—HPO$_4^-$) amino acid residues. The peptide represents the postulated active part of bone sialoprotein (BSP) in controlling bone HAP nucleation and crystal growth modification.

Our preliminary results presented here, suggests stronger peptide attachment on the (0001) surface than the (1010) surface of HAP for both glutamate and protonated phosphoserine sites. Further, there is no preference of either group for adsorption.

Equilibrating peptide in solution shows that HA will possibly preferentially nucleate at the site containing glutamate groups, with a minimum number of eight glutamate sites required in the peptide structure for nucleation to take place.

Example 3

Pharmacokinetics and Bioavailability Study

A group of 40 menopausal women subjects (acting as their own control) ranging in age from 40 to 65 were selected. Clinical studies, which were conducted at the University of Wisconsin Medical School (Madison, Wis.), followed all Institutional Review Board (IRB) protocols and patient confidentiality procedures. In this study (See table below), a composition of this invention was compared against OsCal®, an available calcium supplement commercially available from Merk. The same group of menopausal females functioned as control group in the study. The study was conducted in two phases, the first one being the control phase using OsCal and the second phase being where a product of this invention was administered. Subjects were required to avoid all dairy products or supplements for two weeks and to fast overnight prior to commencement of the study. Subjects were administered 500 mg of a compound of this invention vs. 500 mg of OsCal, with breakfast. Blood samples were drawn at 0, 1, 2, 3, 5, 7 and 9 hour intervals to establish baseline blood calcium and minerals levels over a period of time. A compound of this invention was found to be absorbed in the blood stream, was determined safe to the subjects, with no adverse reactions or detrimental side effects. The results showed OsCal subjects had calcium in their blood serum. However, while invention compound subjects had calcium in their blood serum, the results showed the presence of mineral nutrients known to be important to bone formation. This study established the absorption and safety of a compound of this invention.

|  | OsCal ® | Invention | p |
|---|---|---|---|
| Calcium Cmax (mg/dl) | 0.47 ± 0.25 | 0.43 ± 0.234 | 0.57 |
| Serum calcium Tmax (hr) | 3 § | 3 | 0.87 |
|  | (2, 5) | (1, 5) |  |
| Mean change in serum: |  |  |  |
| Calcium AUC (mg-hr/dl) | 1.67 ± 2.32 | 1.25 ± 1.96 | 0.54 |
| Phosphate (mg/dl) | −0.10 § | 0.40 | 0.006 |
|  | (−0.3, 0.15) | (0.00, 0.675) |  |
| Potassium (mEq/L) | 0.01 ± 0.34 | 0.20 ± 0.20 | 0.08 |
| Magnesium (mg/dl) | 0.01 ± 0.09 | 0.04 ± 0.10 | 0.29 |
| Iron (mcg/dl) | 3.55 ± 13.40 | 6.53 ± 14.35 | 0.52 |

Example 4

NTx Performance Study (Biomarker for Bone Loss)

Thirteen menopausal women age 50 to 71 completed this bone restoration study. NTx is a urinary assay for the measurement of the excretion of cross-linked N-Teleopeptides of Type I Bone Collagen. Bone formation and resorption is normal with a degree of collagen present in urine for disposal of collagen waste. The presence of abnormally high levels of Type 1 Collagen in the urine is an indication of bone loss.

All subjects were initially measured for their NTx readings to establish their baseline status. A normal NTx is a reading below 38 nanomolecules of collagen in urine (nMBCE), Elevated NTx levels are; 38 to 60, High NTx levels are above 60. Normal pre-menopausal women have a reading of about 38. Participant subjects' NTx measurements ranged from 43 to 79. The subjects were administered 2 grams of a compound of this invention in powder form dissolved in at least four ounces of water twice daily for ninety days. At the end of the study period, the subjects were retested for the presence and levels of NTx. Post-study NTx results ranged from 33 to 38 nMBCE, indicating that 100% of the study participants were normalized to healthy NTx levels. Results from the study showed subjects with the highest NTx readings indicating high risk factors for fractures, benefited the most from the therapy of the invention. We believe that these results indicate that compounds of this invention are effective in significantly reducing loss of Type 1 Collagen found in urine.

Example 5

Clinical Practice Study (Bone Mass Development-BMD)

Post-menopausal women recruited from a hospital clinic and a nearby nursing home. These women were screened for Osteoporosis risk factors. The screening was done with the aid of Quantitative Ultra sound (QUS) using Achilles Insight (Lunar GE Medical). Women with a T-Score measurement of minus 2.5 (−2.5) were referred for DXA (Dual X-Ray Absorpotiory) measurement for diagnosis and confirmation.

The Study: One Hundred postmenopausal women were administered with a compound of the invention and screened for improvement in bone health at the end of one year. Results from the study indicate most (87) participants showed improvement in their QUS reading within one year. The study participants continued the therapy for an additional year and completed the study. A preliminary and on-going data analysis indicates that most patients have gained bone mass at a rate in the range of about 5-6% per year over time of the study 2 years. Some participants have shown more significant improvements.

Bone resorption or bone breakdown was measured using the urine NTx assay (Osteomark, Princeton, N.J.). NTx levels were assessed before treatment (baseline) and after twelve weeks of treatment (final). The mean pre-menopausal score or NTx bone resorption is 38 nMBCE.

Table 3/3a presents the data on bone resorption changes at twelve weeks compared to baseline. Eleven out of thirteen subjects had baseline NTx readings from 43 to 60 ('Elevated NTx Group') and the other two subjects had baseline readings above 60 ('High NTx Group'). The subjects in the high NTx baseline group were ages seventy and seventy-one respectively, while the elevated NTx baseline group ranged from ages forty to sixty-nine. All thirteen subjects experienced a reduction in NTx marker of bone resorption. Twelve out of thirteen subjects had a final NTx reading of 37 or 38 (pre-menopausal mean), however, one subject had a final NTx score of 33. Percentage change of baseline for the subjects ranged from −47.94% to −13.63% with the most reduction noted with the subjects in the high NTx baseline group.

Osteoporosis is a disease involving a pathologic bone remodeling process resulting in a shift toward increased osteoclastic activity and decreased osteroblastic activity leading to a net bone loss, resulting in an increased risk of fractures. This phenomenon normally occurs in women during and following menopause. Such bone resorption is seen with excretion of NTx in urine and can easily be measured to observe and modify treatment. In the study, baseline urine NTx measurements above 38 nMBCE were indicative of abnormal bone resorption with a subset of the group in the 'High NTx' category i.e. the group at a relatively higher risk of fractures.

Bone remodeling is a complex process dictated by both organic and inorganic factors. The deficiency of these factors over a period of time leads to abnormal bone resorption and eventual bone loss. Hexamenicol contains both organic and inorganic components, which serve as "raw materials" for building and maintaining bone. The inorganic components are precursors of calcium hydroxyapatite (see Table 1), and the organic components include milk serum basic proteins (MSBP), bone morphogenic proteins, casein phosphopeptides which are the building blocks for type 1 collagen and proteins which also facilitate absorptions, transportation and adhesion for the formation of bone material. This compound also contains carbohydrates, essential fatty acids and vitamins. Several studies have shown that milk basic proteins, MBP promote bone formation.

The subjects in the study, after treatment with OstiGen for twelve weeks, showed a reduction in urine NTx levels to the premenopausal mean of 38 nMBCE, which is an indication that their bone resorption at the end of the study was equivalent to bone formation. Baseline at 38 nMBCE 30 nMBCE/creatinine. One of the subjects had an NTx reading of 33 nMBCE, a value much lower than the pre-menopausal mean. This may be attributed to a phenomenon called 'bone turnover suppression'. The highest percentage changes of baseline were seen with the older subjects (ages 69 to 71 years) recording a range from −36.66% to −47.94%. This subset with the highest relative NTx values had the most benefit granted during this study. DXA is the standard for testing 'bone mineral density' (BMD) but does not measure the quality of the bone. Continued loss of type 1 collagen, especially in the elderly and increase of the mineral matrix because of calcium supplementation gives normal BMD readings but bone becomes brittle and shatters in the event of a fall. One of the objectives of this invention is to maintain the ratio of mineral matrix (65%) and organic matrix (35%) in order to prevent illness, injury and fractures. Quantitative Ultra-Sound (QUS) provides not only the BMD readings but also the quality of the bone mass. In addition to QUS the NTx testing and Bone Alkaline Phosphatase (BAP) testing provide a box of tools in the disease management of Osteoporosis in addition to DXA.

Direct measurement of the rate of bone loss in a patient with osteoporosis would require at least two measurements of bone mass over a 2-4 year interval. Such a strategy is not practical where it is necessary to decide whether or not to treat at the time of initial assessment. Since the rate of bone loss is proportional to the rate of bone turnover in postmenopausal women, it has been suggested that the rate of loss can be predicted by assessing bone turnover that are specific for bone resorption. Although rates of loss assessed in this manner are less accurate than rates of loss assessed over many years by sequential bone mineral density (BMD) measurements, a high rate of bone resorption above the premenopausal mean is associated with a 2-fold increase risk of vertebral and hip fracture independently of the prevailing BMD. The study revealed the resolution of abnormal bone resorption to premenopausal levels with the use of Hexamenicol, indicating that the presumed on-going bone resorption/bone loss was reversed.

The use of this invention over a twelve-week period by menopausal and postmenopausal subjects showed a decreased level of bone resorption. The group at the most risk for fractures had the greatest benefit in achieving a decrease to normal bone resorption levels. The subjects at relatively minimal risk for fractures also benefitted with delayed bone loss. The continued use of Hexamenicol, containing bone building precursors, appears to slow bone loss and shows great promise in helping to build bone which over time will be evident on BMD measurements.

Example 6

Informal Case Study

Chapel Hill, N.C.

A group of women who were diagnosed with osteoporosis with a T-score of −2.5 or lower were prescribed an anti-resportive agent, Fosamax which is a bisphosphonate. It was recommended that they also take calcium supplement with Vitamin D.

A group of seven women received Fosamax and Hexamenicol in place of Calcium and Vitamin D. Another group of women were in the routine treatment of Fosamax, calcium and Vitamin D. NTx tests were conducted on a monthly basis to monitor the progress of the treatment for three months for both groups. The results clearly indicated that all the patients who were on Hexamenicol and complied with the treatment regimen benefitted with normal NTx readings within 3 months, whereas in the Calcium supplement group only 67% of the patients showed improvements in 3 months. This leads us to believe that Hexamenicol could work well in conjunction with Bishosphanates to produce good results in addressing osteoporosis issues.

Example 7

Equine Applications

In the equine athletics it is intended for bone mass building, Bone growth, Bone repair and maintenance of the skeletal structure. It is particularly well suited for the racing industry where an offspring which is born any month of the year is considered one year old and are subjected to training in a very young age before the full bone mass and skeletal structure is attained to withstand the rigorous training resulting in serious injury.

In a race track barn a 2 year old expensive colt sustained a serious canon bone injury resulting in a surgery where the fractured canon bone was reattached by drilling a hole in the bottom of the fracture and top of the fractured bone and secured with a pin. The leg then was immobilized and the colt was administered 30-60 grams of Hexamenicol. The new compound was sprinkled on top of the grain ration twice a day of 15-30 grams per treatment. The colt had no problem consuming Hexamenicol and no side reactions were noted during the entire treatment period. At the end of month 1 treatment there were no significant improvements noticed in the x-rays. The treatment continued and at the end of month 2 substantial formation of bone was noticed in the x-rays. The trainer and the veterinary surgeon felt that calcification is taking place at a rapid rate. The treatment was continued and the end of 3 months there was a complete healing of the canon bone resulting in a much stronger bone structure than the normal unbroken leg. The colt was back in training full scale and participated in a race, placing second at the 4th month. The trainer quoted, "In all my 40 years of training I have never seen such a complete healing of the canon bone injury as I have seen in this colt." Further experiments concluded that this is a viable option to provide this preparation to pregnant mares, weaned colts and fillies, young adults in training and among mature animals in maintenance of bone, muscle and tendon tissues. This preparation is a viable option for animals facing steroid treatment and also benefit in the process of bone loss due to steroid intake in treatments.

Example 8

Canine Applications

Hexamenicol is found to be an effective treatment option for sports animals, show dogs and working dogs for treatment of bone fracture healing, in hip dysplasia and skeletal growth. It is found to be a valuable option for maintenance of bone strength and bone density. Several batches of dog biscuits were made with the objective of providing 1.5 to 2 grams of Hexamenicol on a daily basis. The trial animals preferred the biscuits made with Hexamenicol and did not have any side reactions. The trial animals maintained normal roles and further studies are planned in this area.

Example 9

Avian and Poultry Applications

Laying hens were fed in their daily ration of 120 mgs per 7 lbs in average weight birds of our compound for 3 months and found the thickness and stability of egg shells and the firmness of the egg yolk and egg white were superior to control groups who were on a normal daily ration. This leads us to believe that our compound has application in poultry industry to maintain the blood serum calcium and other mineral nutrients to produce healthy eggs. It is also applicable to the Avian breeding programs for captive pet and zoo industry birds and has critical application in endangered species rejuvenation programs.

The following References are incorporated by reference herein as though they are part of this Application.

REFERENCES

1. NOF Fast facts on osteoporosis: Disease Statistics. National Osteoporosis Foundation. February 2003.
2. Siris E S, Miller P D, Barrett-Connor E, et al. NORA. Identification and fracture outcomes of undiagnosed low bone mineral density in postmenopausal women: Results from the National Osteoporosis Risk Assessment. JAMA. Dec. 12, 2001; 286(22):2815-2822.
3. Bayne A. Osteoporosis remains under-diagnosed in the United States. Review of National Osteoporosis Risk Assessment (NORA). Eureka Alert. 2001.
4. U.S. Dept. of Health & Human Services. Bone Health and Osteoporosis. A Report of the Surgeon-General, Rockville, Md.: 2004.
5. Kalkwarf H J, Khoury J C, Lanphear B P. Milk intake during childhood and adolescence, adult bone density and osteoporotic fractures in U.S. women. Am J Clin Nutr. 2003; 77: 257-265.
6. Renner E, Hermes M, Starke H. Bone mineral density of adolescents as affected by calcium intake through milk and milk products. Int Dairy J. 1998; 8: 759-764.
7. Heaney R P. Calcium, dairy products and osteoporosis. J Am Coll Nutr. 2000; 19(2): 83S-99S.
8. Holick M F, Dawson-Hughes B (eds). Nutrition and bone health. Totowa, N. J. Humana Press 2004; 237-239.
9. Miller G D, Jarvis J K, McBean L D. Handbook of dairy foods and nutrition, $2^{nd}$ Ed. Boca Raton Fla.: CRC Press, 2000.
10. Aoe S, Toba Y, Yamamura J, et al. Controlled trial of the effects of milk basic protein (MBP) supplementation on bone metabolism in healthy adult women. Biosci Biotechnol Biochem. 2001; 65(4): 913-918.
11. Yamamura J, Aoe S, Toba Y, et al. Milk basic protein (MBP) increases radial bone mineral density in adult women. Biosci Biotechnol Biochem. 2002; 66(3): 702-704.
12. Celotti F, Bignamini A. Dietary calcium and mineral/vitamin supplementation: A controversial problem. J Int Medical Res. 1999; 27: 1-14.
13. Swaminathan R. Nutritional factors in osteoporosis. Int J Clin Practice. 1999; 53: 540-548.
14. McBean L D. Building better bones with dairy foods throughout the life cycle. Diary Council Digest 2004; 75(6): 31-36.
15. Toba Y, Takada Y, Yamamura J, Tanaka M, et al. Milk basic protein: A novel protective function of milk against osteoporosis. Bone. 2000; 27(3): 403-408.
16. Prentice A, Bates CJ. Adequacy of dietary mineral supply for human bone growth and mineralisation. Eur J Clin Nutr. 1994; 48 suppl 1: S161-176; discussion 5177.
17. Noat D, Grey A, Reid I R, Cornish J. Lactoferrin: A novel bone growth factor. Clin Med. Res. 2005; 3(2): 93-101.
18. Matsuoka Y, Serizawa A, Yoshioka T, Yamamura J, et al. Cystatin C in milk basic protein and its inhibitory effect on bone resorption in vitro. Biosci Biotechnol Biochem. 2002; 66(12): 2531-2536.
19. Schlimme E, Meisel H. Bioactive peptides derived from milk proteins: Structural, physiological and analytical aspects. Die Nahrung. 1995; 39: 1-20.
20. Scholz-Ahrens K E, Schrezenmeir J. Effects of bioactive substances in milk on mineral and trace element metabolism with special reference to casein phosphopeptides. Br J. Nutr. 2000; 84 suppl 1: S147-153.
21. Hanson D A. A specific immunoassay for monitoring human bone resorption: Quantitation of Type I collagen cross-linked N-telopeptides in urine. J Bone Miner Res. 1992; 7(11): 1251-1258.
22. Schneider D L. Urinary N-telopeptide levels discriminate normal, osteopenic and osteoporotic bone mineral density. Arch Intern Med. 1997; 157(11): 1241-1245.
23. Kanis J A, Delmas P, Burckhardt P, Cooper C, Torgerson D. Guidelines for diagnosis and management of osteoporosis. Osteoporosis Int. 1997; 7: 390-406.
24. Osteomark NTx. Princeton N. J. Product background information.
25. Minisola S. Bone turnover and its relationship with bone mineral density in pre- and postmenopausal women with or without fractures. Maturitas. 1998; 29(3): 265-270.
26. Rogers A, Hannon R, Eastell R. Biochemical markers as predictors of rates of bone loss after menopause. J Bone Miner Res. 2000; 15(7): 1398-1404.
27. Bauer D C, Sklarin P M, Stone K L, Black D M, Nevitt M C, Ensrud K E, at al. Biochemical markers of bone turnover and prediction of hip bone loss in older women: The study of osteoporotic fractures. J Bone Miner Res. 1999; 14(8): 1404-1410.
28. Rosen C J, Tenenhouse A. Osteoporosis Symposium: Biochemical markers of bone turnover. Postgraduate Medicine. 1998; 104(4).
29. Cotran R, Kumar V, Collins T, Robbins S. Pathological basis of disease. Chapter: Skeletal system and soft tissue tumors: Bones. $6^{th}$ Ed. WB Saunders: 1999.
30. Corral D A, Amling M, Priemel M, et al. Dissociation between bone resorption and bone formation in osteopenic transgenic mice. Proc Natl Acad Sci USA. 1998; 95 (23): 13835-13840.
31. Wactawski-Wende, J, Ph.D., Morley Kotchen, J, M.D., Anderson, GL, Ph.D, et al. Calcium plus Vitamin D Supplementation and the Risk of Colorectal Cancer New England Journal of Medicine, Volume 354:684-696, Feb. 16, 2006, Number 7.
32. Kruger, M C et al., The Effect of Whey Acidic Protein Fractions on Bone Loss in the Ovariectomised Rat, British J. of Nutrition (2005), 93, 244-252.
33. Illich, J Z et al., "Nutrition in Bone Health Revisited: A Story Beyond Calcium, J. of American College of Nutrition, Vol., 19, No. 6, 715-737 (2000).

What is claimed is:

1. A nutritional composite material made according to a process comprising the steps of:
    (a) providing whey-derived milk minerals in solid form;
    (b) providing milk-derived proteins in solution;
    (c) exposing the milk-derived protein solution of step (b) to an ion exchange or filtration step to produce a solution comprising acidic proteins and enhanced-weight percent milk-derived basic proteins;
    (d) removing sodium-based minerals and sodium salts from the milk-derived protein solution of step (c);
    (e) purifying the whey-derived solid minerals of step (a) by mixing the minerals with a solvent and heating the resulting solution;
    (f) combining the purified whey-derived solid mineral solution of the previous step with the milk-derived protein solution of step (d); and
    (g) removing the solvent of the previous step to produce the nutritional composite material.

Figure 18:
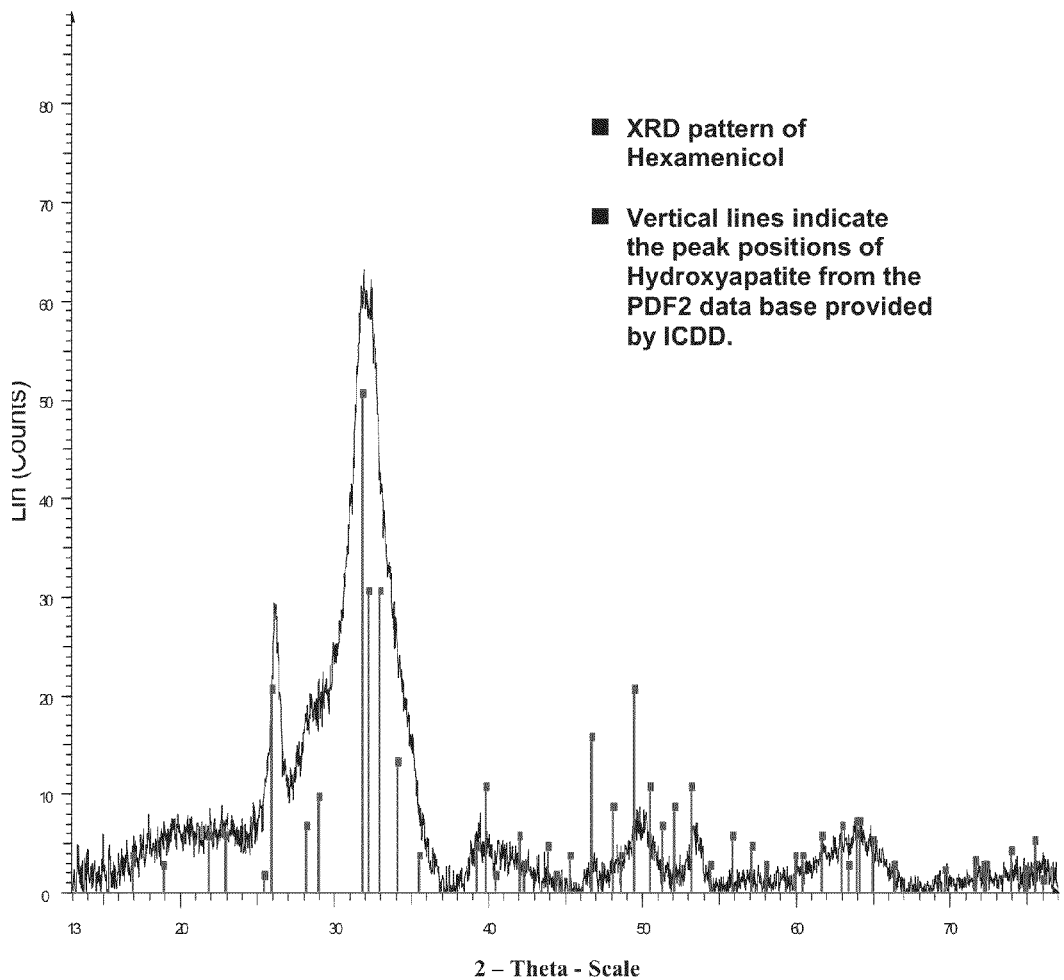
FIG. 18 is the XRD pattern of Hexamenicol a compound of this invention. The vertical lines indicate the peak positions of hydroxyapatite from the PDF2 database provided by ICDD.
Figure 19:
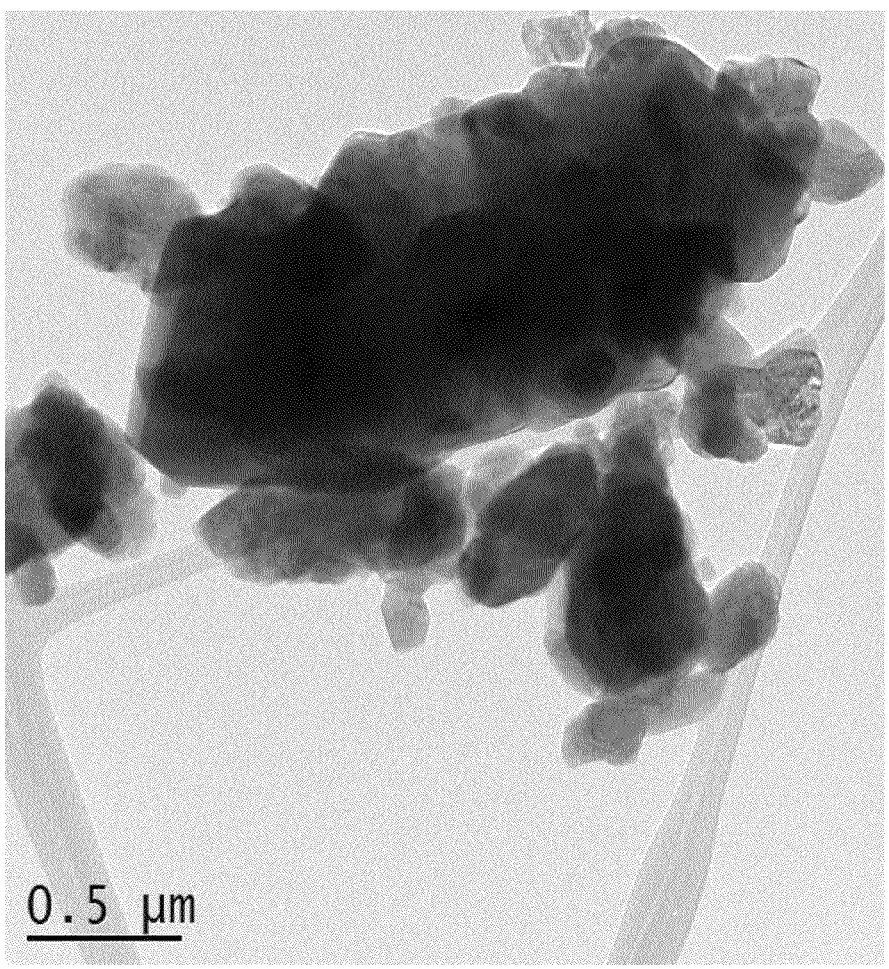
FIGS. 19 and 20 is a low-magnification TEM (transmission electron microscope) image showing calcium carbonate crystals and their aggregates. Crystal size ranges from 200 nm to 2 microns in a single direction.
Figure 20:
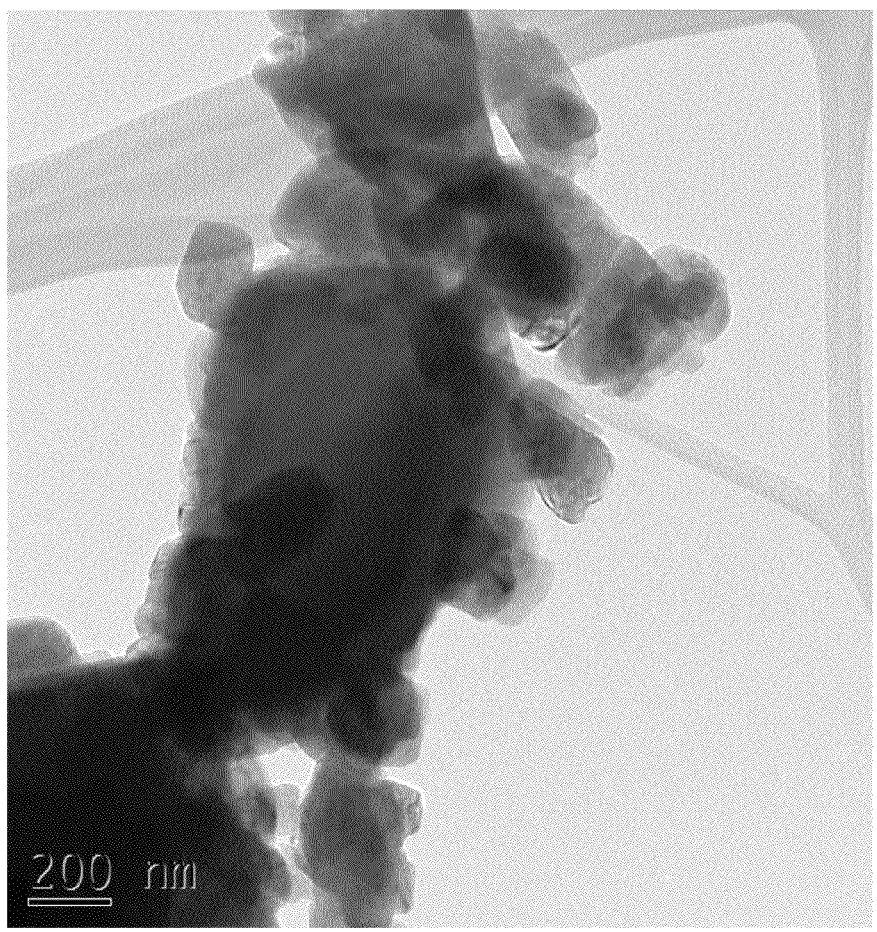
Figure 21:
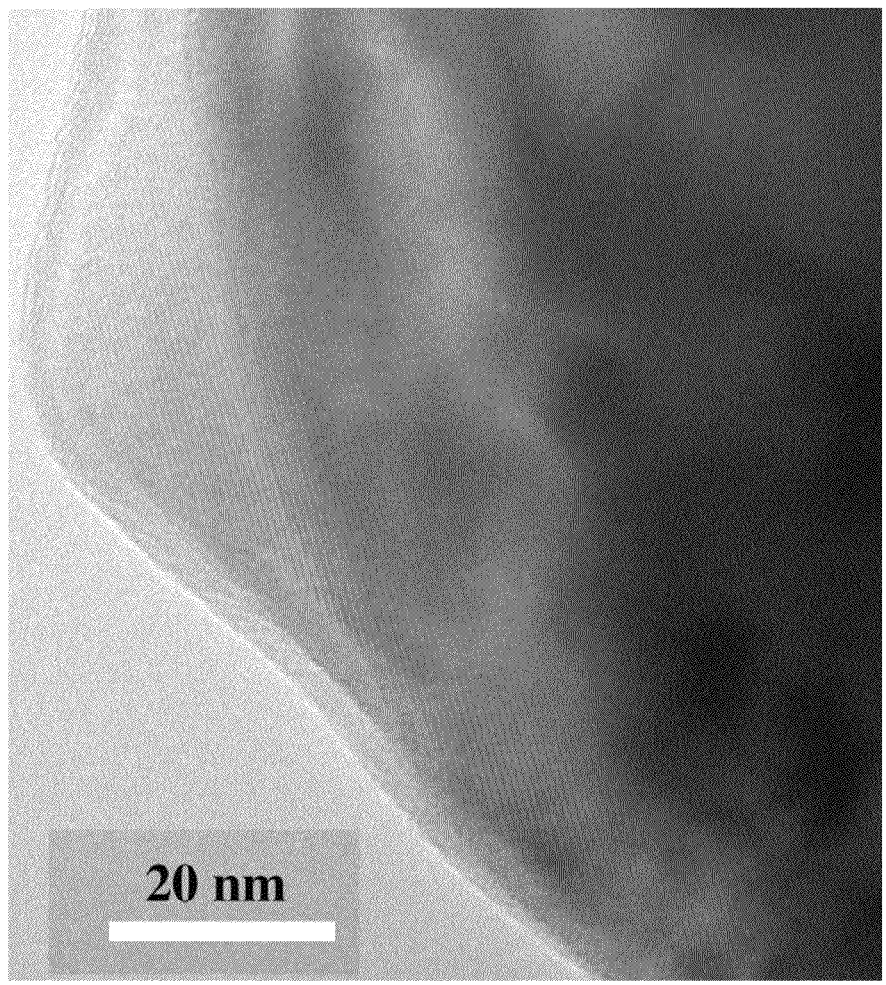
FIGS. 21 and 22 show high magnification TEM images showing lattice fringes in a calcium carbonate crystal, formation in a single direction.
Figure 22:
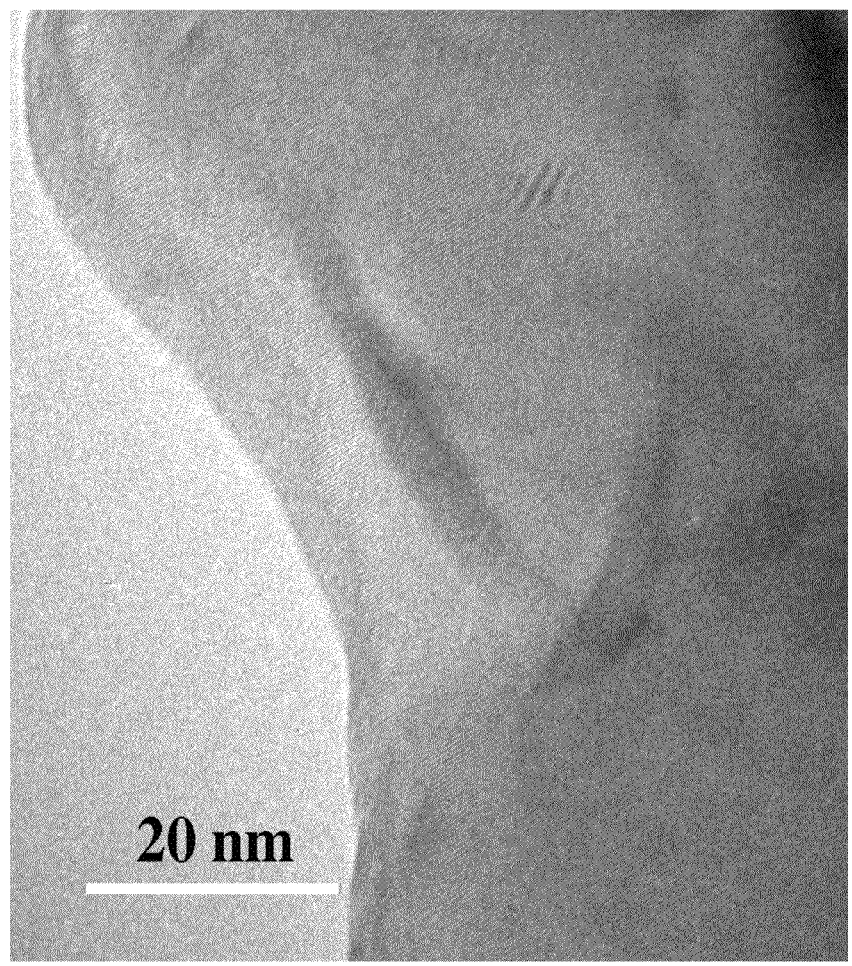
Figure 23:
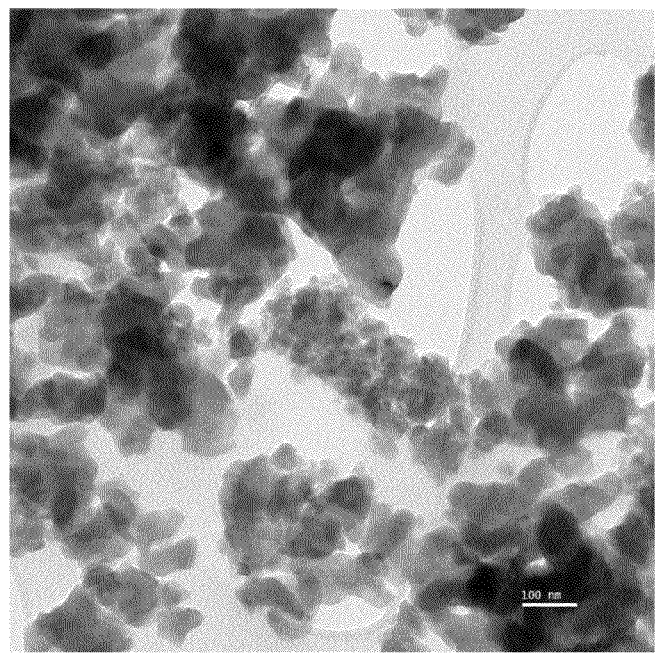
FIGS. 23 and 24 are low-magnification TEM images of synthetic hydroxy apatite crystals and their aggregates (synthetic hydroxy from Aldrich Chemical, St. Louis, Mo. U.S.A.). Crystal size ranges from 50 nm to 100 nm.
Figure 24:
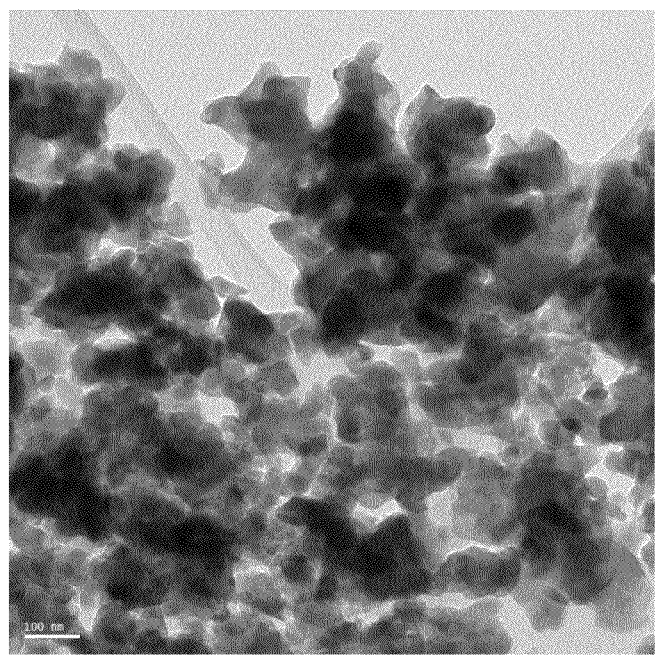
Figure 25:
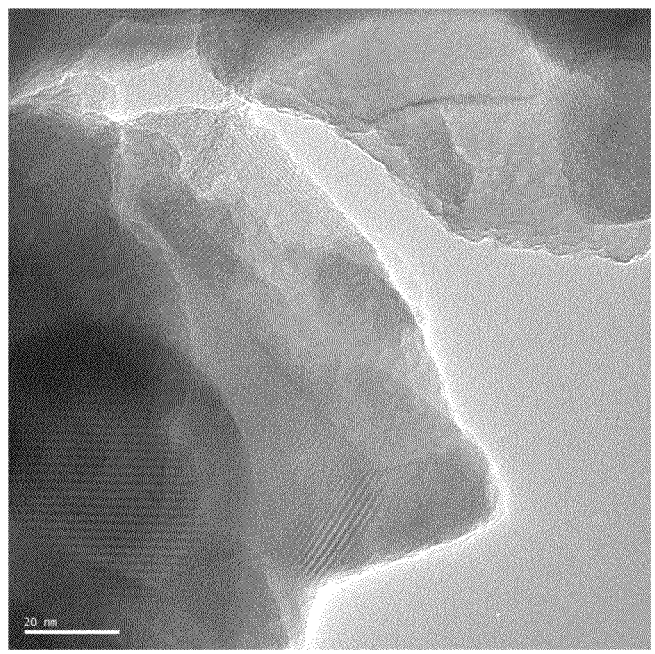
FIGS. 25 and 26 are high magnification TEM images of synthetic calcium hydroxyapatite from Aldrich chemicals showing lattice fringes in the apatite crystals in a single direction.
Figure 26:
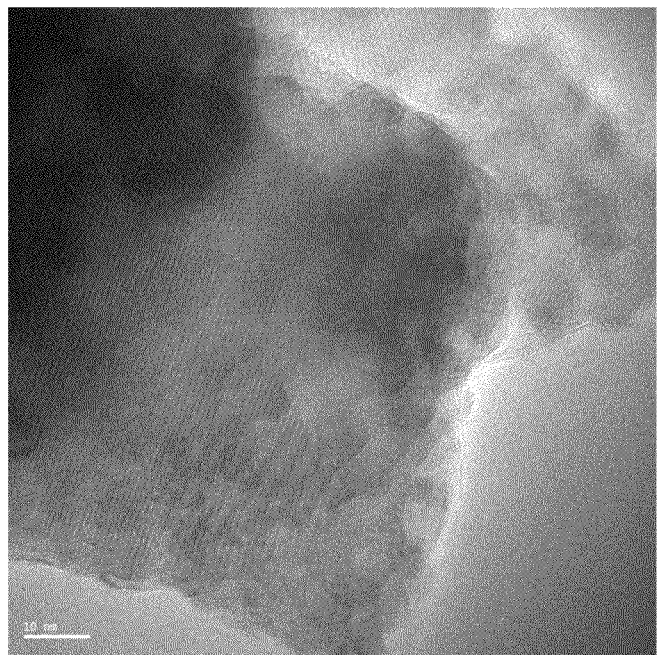
Figure 27:
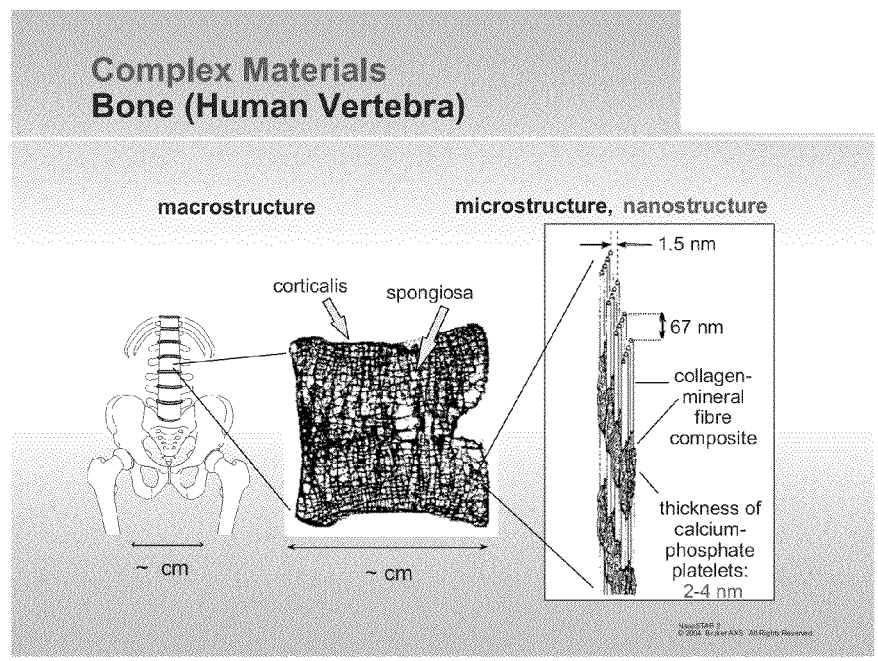
FIG. 27 shows a detailed macrostructure and microstructure of human vertebra showing the relative average sizes of the indicated structures. Hexamenicol resembles the nanostructure of the bone when rolled.
Figure 28:
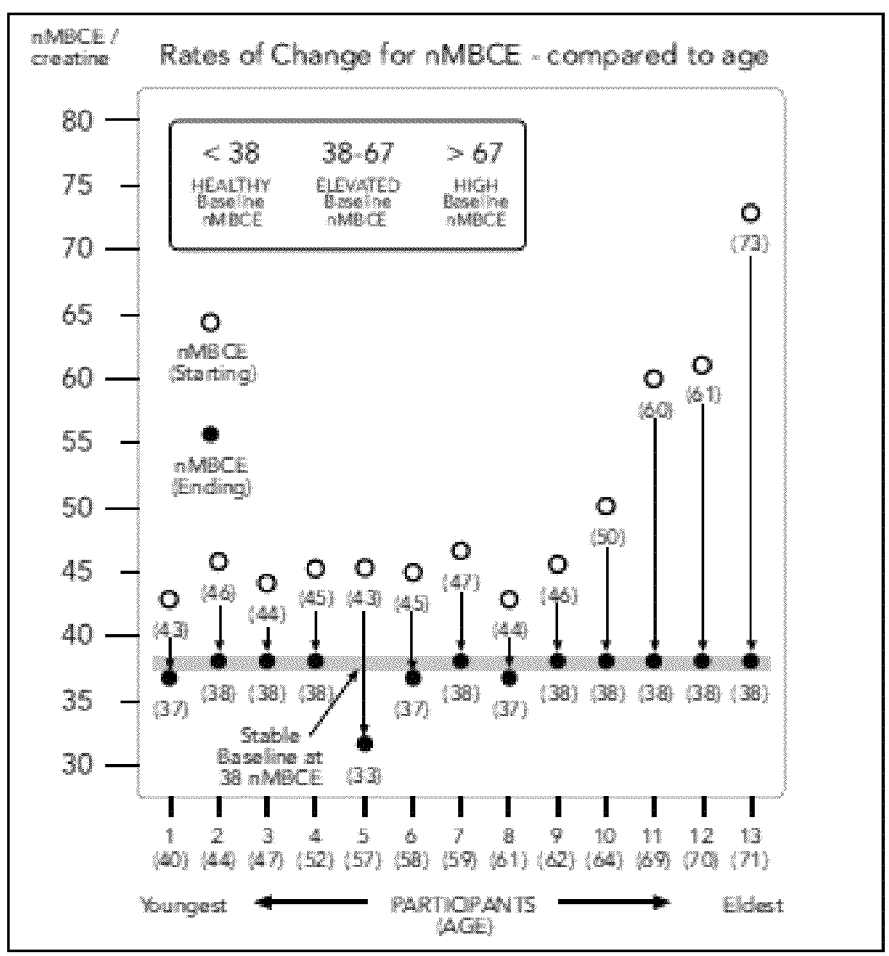
FIG. 28 shows the rate of change for nmBCE as compared to age for the participants in Table 3.

2. The nutritional composite material of claim 1 comprising an x-ray diffraction pattern as shown in FIG. 18.

3. A nutritional composite material comprising whey-derived milk minerals and specific proteins that are acidic and basic in nature, whereby the nutritional composite material has the X-ray diffraction pattern shown in FIG. 18 when subjected to X-ray diffraction analysis.

4. The nutritional composite material of claim 3 further comprising one or more growth factors.

5. The nutritional composite material of claim 4 further comprising lactoferrin and lactoperoxidase.

6. The nutritional composite material of claim 5 further comprising bone morphongenic proteins.

7. The nutritional composite material of claim 6 further comprising a protein selected from the group consisting of: alpha-lactalbumin, beta-lactglobulin, and immuno-gamma globulin.

* * * * *